US012642610B2

(12) United States Patent
Crawford et al.

(10) Patent No.: US 12,642,610 B2
(45) Date of Patent: Jun. 2, 2026

(54) SYSTEM AND METHOD FOR SURGICAL TOOL INSERTION USING MULTIAXIS FORCE AND MOMENT FEEDBACK

(71) Applicant: GLOBUS MEDICAL, INC., Audubon, PA (US)

(72) Inventors: Neil R. Crawford, Chandler, AZ (US); Norbert Johnson, North Andover, MA (US)

(73) Assignee: Globus Medical Inc., Audubon, PA (US)

( * ) Notice: Subject to any disclaimer, the term of this patent is extended or adjusted under 35 U.S.C. 154(b) by 69 days.

(21) Appl. No.: 18/883,430

(22) Filed: Sep. 12, 2024

(65) Prior Publication Data

US 2025/0072983 A1     Mar. 6, 2025

Related U.S. Application Data

(63) Continuation of application No. 17/317,344, filed on May 11, 2021, now Pat. No. 12,133,699, which is a
(Continued)

(51) Int. Cl.
*A61B 34/30* (2016.01)
*A61B 5/06* (2006.01)
(Continued)

(52) U.S. Cl.
CPC .............. *A61B 34/30* (2016.02); *A61B 5/064* (2013.01); *A61B 17/1604* (2013.01); *A61B 17/1626* (2013.01); *A61B 17/7082* (2013.01); *A61B 17/8875* (2013.01); *A61B 34/20* (2016.02); *A61B 90/96* (2016.02); *A61B 90/98* (2016.02); *A61B 2017/00022* (2013.01); *A61B*

*2017/00115* (2013.01); *A61B 2017/00119* (2013.01); *A61B 2017/00477* (2013.01); *A61B 2017/00876* (2013.01); *A61B 17/1671* (2013.01); *A61B 17/1757* (2013.01); *A61B 2034/2051* (2016.02); *A61B 2034/2055* (2016.02); *A61B 2034/2057* (2016.02); *A61B 2034/2072* (2016.02); *A61B 2090/034* (2016.02); *A61B 2090/062* (2016.02);
(Continued)

(58) Field of Classification Search
CPC ......... A61B 34/30; A61B 34/20; A61B 90/96; A61B 90/98; A61B 5/064; A61B 17/1604; A61B 17/1626; A61B 17/7082; A61B 17/8875
USPC ................................... 606/1, 80, 130, 96–98
See application file for complete search history.

(56) References Cited

U.S. PATENT DOCUMENTS 4,663,955 A * 5/1987 Redman ................... B21D 3/04
72/160
5,820,546 A * 10/1998 Ouchi ............... A61M 25/0662
600/153
(Continued)

*Primary Examiner* — Jessica Weiss

(57) ABSTRACT

Devices, systems, and methods for providing a degree of freedom to a guide tube associated with a robotic surgical system. The surgical robot system may be configured to have six degrees of freedom associated with a vertical lift, rotation about a shoulder, rotation about an elbow, roll of a forearm, pitch of the end-effector, and rotation of a guide tube independent from the end-effector. The robotic surgical system allows for the proper orientation of an instrument in the guide tube along a trajectory to the operational site of a patient.

8 Claims, 25 Drawing Sheets

Related U.S. Application Data continuation-in-part of application No. 17/098,958, filed on Nov. 16, 2020, now Pat. No. 11,950,865, which is a continuation of application No. 15/652,914, filed on Jul. 18, 2017, now Pat. No. 10,874,466, which is a continuation-in-part of application No. 15/371,304, filed on Dec. 7, 2016, now Pat. No. 10,646,280, which is a continuation-in-part of application No. 15/157,444, filed on May 18, 2016, now Pat. No. 11,896,446, which is a continuation-in-part of application No. 15/095,883, filed on Apr. 11, 2016, now Pat. No. 10,893,912, which is a continuation-in-part of application No. 14/062,707, filed on Oct. 24, 2013, now Pat. No. 10,357,184, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | |
|---|---|
| *A61B 17/16* | (2006.01) |
| *A61B 17/70* | (2006.01) |
| *A61B 17/88* | (2006.01) |
| *A61B 34/20* | (2016.01) |
| *A61B 90/96* | (2016.01) |
| *A61B 90/98* | (2016.01) |
| *A61B 17/00* | (2006.01) |
| *A61B 17/17* | (2006.01) |
| *A61B 90/00* | (2016.01) |
| *A61B 90/11* | (2016.01) |

(52) U.S. Cl.
CPC ... *A61B 2090/064* (2016.02); *A61B 2090/066* (2016.02); *A61B 2090/0811* (2016.02); *A61B 90/11* (2016.02); *A61B 2090/376* (2016.02); *A61B 2090/3762* (2016.02); *A61B 2090/3937* (2016.02); *A61B 2090/3945* (2016.02); *A61B 2090/3983* (2016.02); *A61B 2505/05* (2013.01); *A61B 2562/02* (2013.01)

(56) References Cited

U.S. PATENT DOCUMENTS

| | | | | |
|---|---|---|---|---|
| 7,643,864 B2 * | 1/2010 | Elgort | .................... | G01R 33/54 |
| | | | | 324/307 |
| 8,986,314 B1 * | 3/2015 | Jordan | .............. | A61B 17/1714 |
| | | | | 606/96 |
| 2005/0228440 A1 * | 10/2005 | Brock | .................... | A61B 34/30 |
| | | | | 606/205 |
| 2007/0034731 A1 * | 2/2007 | Falco | .................... | G01B 11/03 |
| | | | | 342/174 |
| 2008/0039868 A1 * | 2/2008 | Tuemmler | ............ | A61B 90/36 |
| | | | | 606/130 |
| 2008/0064921 A1 * | 3/2008 | Larkin | .............. | A61B 1/00154 |
| | | | | 128/898 |
| 2010/0256558 A1 * | 10/2010 | Olson | .................... | A61B 34/77 |
| | | | | 604/95.01 |
| 2015/0209056 A1 * | 7/2015 | Shoham | ................. | A61B 34/30 |
| | | | | 606/80 |

* cited by examiner

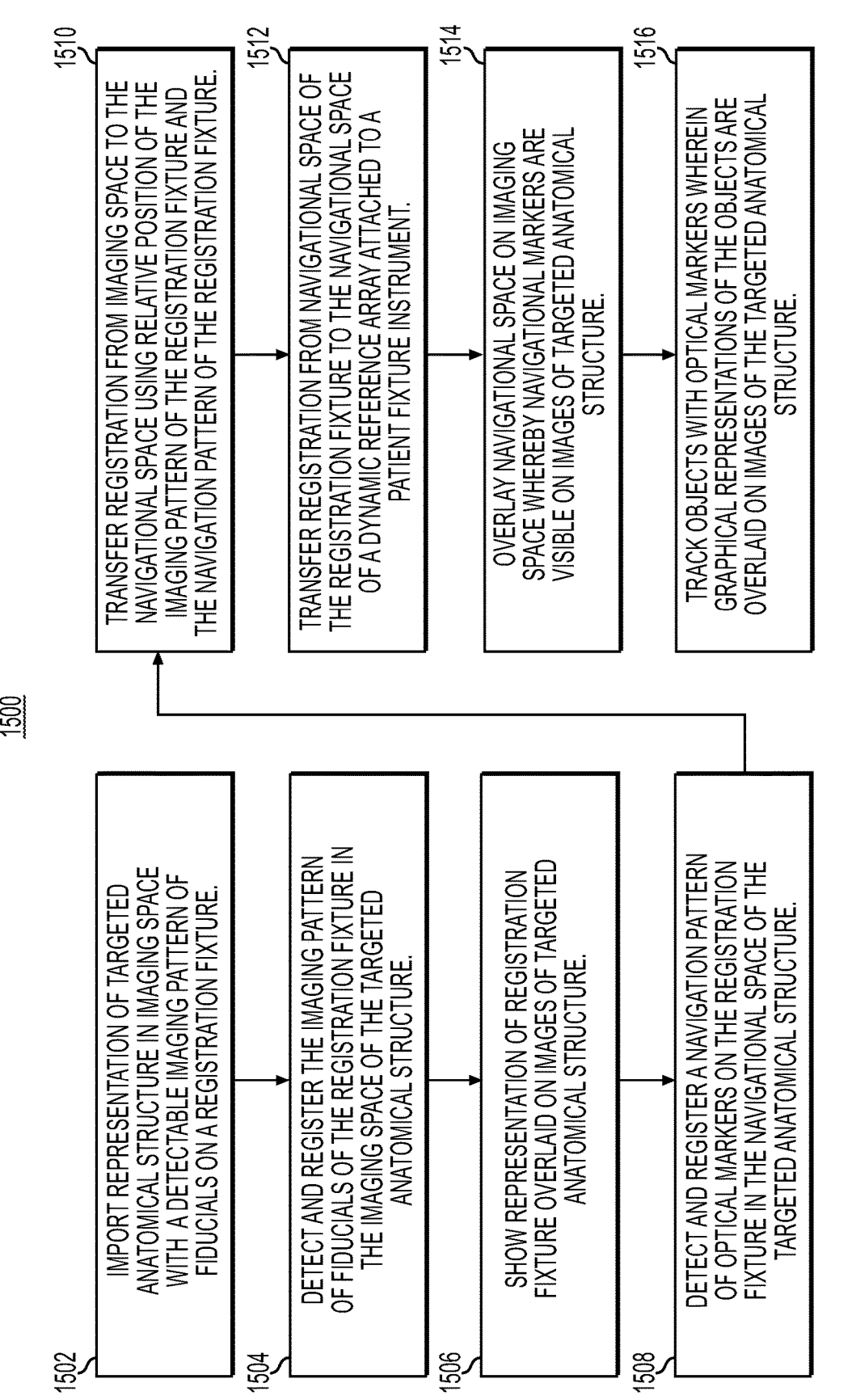

1500

1502 IMPORT REPRESENTATION OF TARGETED ANATOMICAL STRUCTURE IN IMAGING SPACE WITH A DETECTABLE IMAGING PATTERN OF FIDUCIALS ON A REGISTRATION FIXTURE.

1504 DETECT AND REGISTER THE IMAGING PATTERN OF FIDUCIALS OF THE REGISTRATION FIXTURE IN THE IMAGING SPACE OF THE TARGETED ANATOMICAL STRUCTURE.

1506 SHOW REPRESENTATION OF REGISTRATION FIXTURE OVERLAID ON IMAGES OF TARGETED ANATOMICAL STRUCTURE.

1508 DETECT AND REGISTER A NAVIGATION PATTERN OF OPTICAL MARKERS ON THE REGISTRATION FIXTURE IN THE NAVIGATIONAL SPACE OF THE TARGETED ANATOMICAL STRUCTURE.

1510 TRANSFER REGISTRATION FROM IMAGING SPACE TO THE NAVIGATIONAL SPACE USING RELATIVE POSITION OF THE IMAGING PATTERN OF THE REGISTRATION FIXTURE AND THE NAVIGATION PATTERN OF THE REGISTRATION FIXTURE.

1512 TRANSFER REGISTRATION FROM NAVIGATIONAL SPACE OF THE REGISTRATION FIXTURE TO THE NAVIGATIONAL SPACE OF A DYNAMIC REFERENCE ARRAY ATTACHED TO A PATIENT FIXTURE INSTRUMENT.

1514 OVERLAY NAVIGATIONAL SPACE ON IMAGING SPACE WHEREBY NAVIGATIONAL MARKERS ARE VISIBLE ON IMAGES OF TARGETED ANATOMICAL STRUCTURE.

1516 TRACK OBJECTS WITH OPTICAL MARKERS WHEREIN GRAPHICAL REPRESENTATIONS OF THE OBJECTS ARE OVERLAID ON IMAGES OF THE TARGETED ANATOMICAL STRUCTURE.

*FIG. 11*

VERTICAL

SHOULDER

ELBOW

ROLL

PITCH

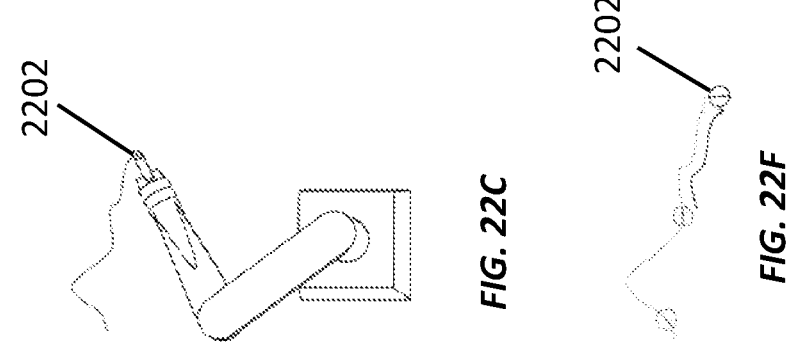
FIG. 22A
FIG. 22B
FIG. 22C
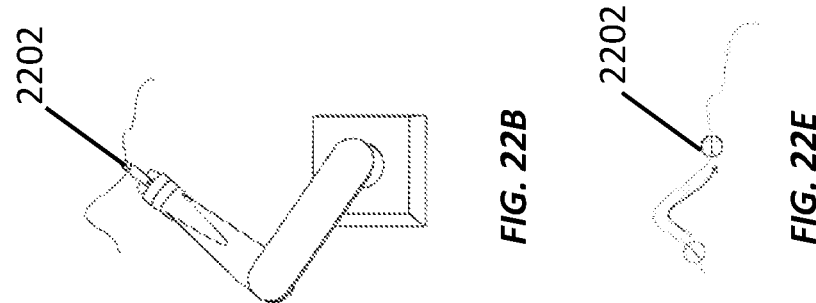
FIG. 22D
FIG. 22E
FIG. 22F

Angle relative to upright

2402

Inertia / gravity sensor

Guide tube

2302

Vertical (gravity) vector

Radial vector (projection) showing direction from inertial sensor toward vertical (gravity) vector Centerline of guide tube

2302

To robot
wrist /
forearm

Six-axis
load cell

2502

SYSTEM AND METHOD FOR SURGICAL TOOL INSERTION USING MULTIAXIS FORCE AND MOMENT FEEDBACK

CROSS-REFERENCE TO RELATED APPLICATIONS

This application is a continuation of U.S. patent application Ser. No. 17/317,344 filed on May 11, 2021, which is a continuation-in-part of U.S. patent application Ser. No. 17/098,958 filed on Nov. 16, 2020, which is a continuation of U.S. patent application Ser. No. 15/652,914 filed on Jul. 18, 2017 (now U.S. Pat. No. 10,874,466), which is a continuation-in-part application of U.S. patent application Ser. No. 15/371,304 filed on Dec. 7, 2016 (now U.S. Pat. No. 10,646,280), which is a continuation-in-part of U.S. patent application Ser. No. 15/157,444 filed May 18, 2016 (published as U.S. Pat. Pub. 2016-0256225), which is a continuation-in-part application of U.S. patent application Ser. No. 15/095,883 filed on Apr. 11, 2016 (now U.S. Pat. No. 10,893,912), which is a continuation-in-part application of U.S. patent application Ser. No. 14/062,707 filed on Oct. 24, 2013 (now U.S. Pat. No. 10,357,184), which is a continuation-in-part application of U.S. patent application Ser. No. 13/924,505 filed on Jun. 21, 2013 (now U.S. Pat. No. 9,782,229), which is a nonprovisional patent application that claims priority to U.S. provisional patent application No. 61/662,702 filed on Jun. 21, 2012, and claims priority to U.S. provisional patent application No. 61/800,527 filed on Mar. 15, 2013, the entire contents of all of which are incorporated herein by reference.

FIELD OF THE INVENTION

The present disclosure relates to improved tool insertion using robot-assisted surgical techniques.

BACKGROUND OF THE INVENTION

Various medical procedures require the accurate localization of a three-dimensional position of a surgical instrument within the body in order to effect optimized treatment. A robotic surgical system may have five degrees of freedom to facilitate accurate positioning of the surgical instrument in relation to the body. These five degrees of freedom from a base of the robotic surgical system to an end effector include: (1) vertical linear motion, (2) shoulder rotation in the horizontal plane, (3) elbow rotation in the horizontal plane, (4) roll of the forearm, and (5) pitch of the end effector. With these five degrees of freedom, it is possible to move the robotic surgical system into a range of positions and angles where it can hold a guide tube to facilitate placement of screws and other straight line trajectories into the body.

These five degrees of freedom allow the guide tube of the end effector to be aligned with a trajectory vector, but the rotational position of the guide tube about the trajectory vector may not be independently selected and is dependent on the positions of these other joints. When using five degrees of freedom in this configuration, the movement of the robot along a straight line approaching the patient is usually associated with some residual rotation of the guide tube during the movement.

Shortcomings of a five degree of freedom robotic system may include an inability of the robot to move the guide tube along a fixed trajectory without residual rotation about the guide tube, an inability to provide active rotational motion to perform surgical tasks such as drilling or inserting screws, and inability to automatically orient a cutting blade while holding the guide tube perpendicular to a surface.

Thus, there is a need to provide an additional degree of freedom for a guide tube associated with a five degree of freedom surgical robotic system. This may be accomplished as noted in the present disclosure using robot-assisted surgical techniques.

SUMMARY OF THE INVENTION

To meet these and other needs, device, systems, and methods for automatically rotating a guide tube are provided.

According to one exemplary embodiment, a surgical robot system having a robot base, a robot arm connected to and in electronic communication with the robot base, an end-effector connected to the robot arm and in electronic communication with the robot base. The end-effector includes guide tube that is configured to receive a surgical instrument. The guide tube is configured automatically rotate about a central axis of the guide tube as the robot arm and end-effector are moved along a trajectory to a surgical site.

According to one exemplary embodiment, a method of moving a surgical robot system relative to a patient. The method includes registering the surgical robot system to an anatomy of the patient. The surgical robot system includes a robot base, a robot arm connected to and in electronic communication with the robot base, and an end-effector connected to the robot arm and in electronic communication with the robot base. The end-effector includes a guide tube and is configured to receive a surgical instrument. The guide tube is configured to automatically rotate about a central axis of the guide tube as the robot arm and end-effector are moved along the trajectory. The method further includes moving the robot arm and end-effector along a trajectory to the anatomy of the patient.

BRIEF DESCRIPTION OF THE DRAWINGS

The invention and the following detailed description of certain embodiments thereof may be understood by reference to the following figures:

FIG. 11 illustrates a method of registration in accordance with an exemplary embodiment;

FIGS. 22A-F illustrates a robotic surgical system consistent with the principles of the present disclosure.

DETAILED DESCRIPTION OF THE INVENTION

Figure 1:
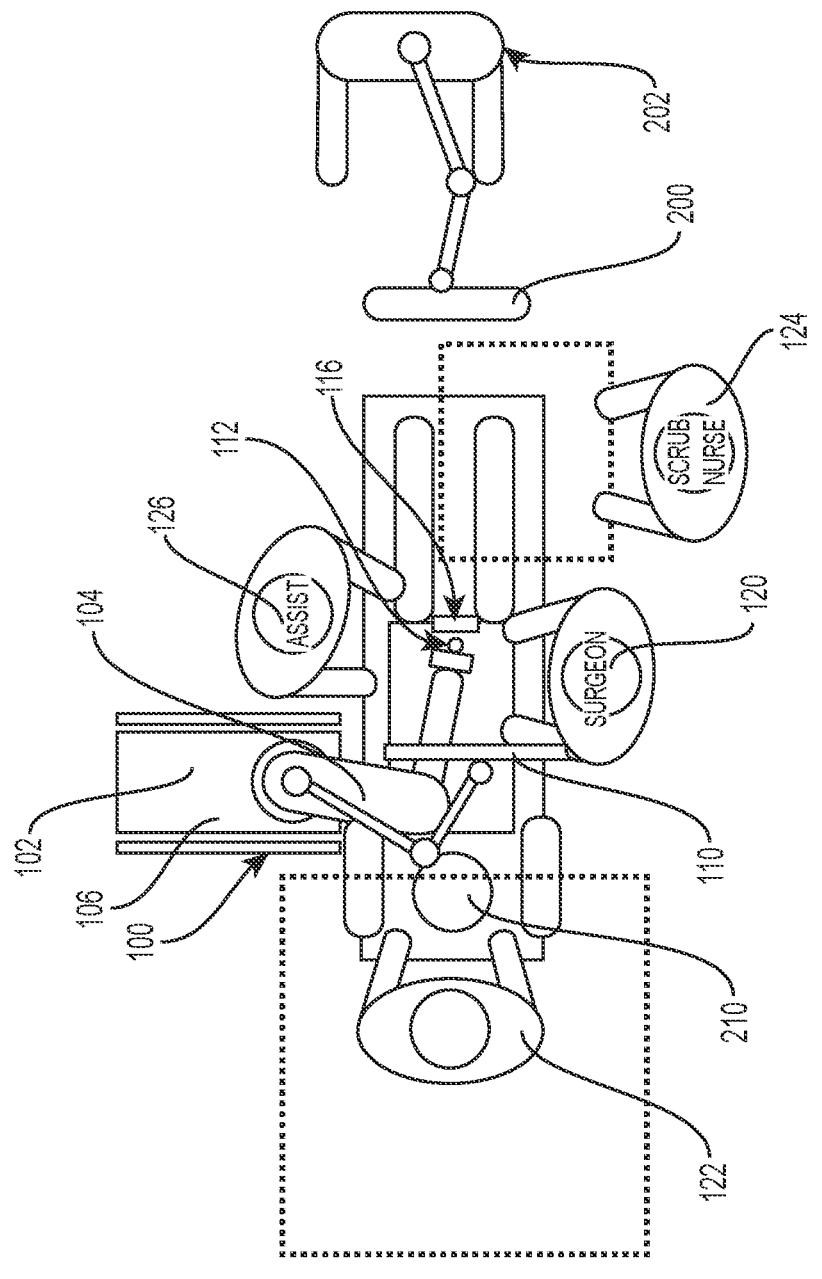
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
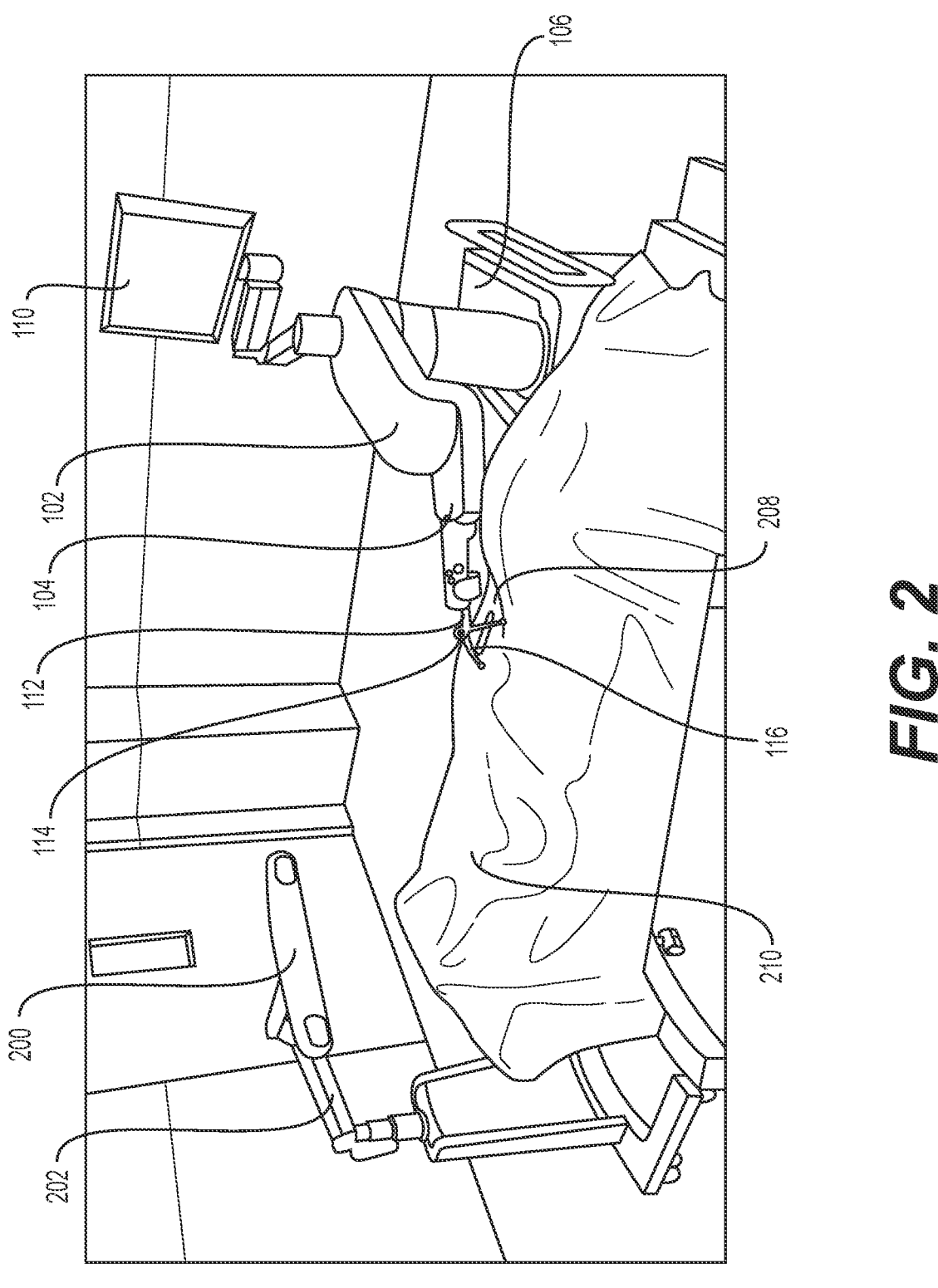
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End effector 112 may be coupled to the robot arm 104 and controlled by at least one motor. In exemplary embodiments, end effector 112 can comprise a guide tube 114, which is able to receive and orient a surgical instrument 608 (described further herein) used to perform surgery on the patient 210. As used herein, the term "end effector" is used interchangeably with the terms "end-effectuator" and "effectuator element." Although generally shown with a guide tube 114, it will be appreciated that the end effector 112 may be replaced with any suitable instrumentation suitable for use in surgery. In some embodiments, end effector 112 can comprise any known structure for effecting the movement of the surgical instrument 608 in a desired manner.

The surgical robot 102 is able to control the translation and orientation of the end effector 112. The robot 102 is able to move end effector 112 along x-, y-, and z-axes, for example. The end effector 112 can be configured for selective rotation about one or more of the x-, y-, and z-axis, and a Z Frame axis (such that one or more of the Euler Angles (e.g., roll, pitch, and/or yaw) associated with end effector 112 can be selectively controlled). In some exemplary embodiments, selective control of the translation and orientation of end effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end effector 112 and/or the surgical instrument 608. Thus, in use, in exemplary embodiments, a physician or other user can operate the system 100, and has the option to stop, modify, or manually control the autonomous movement of end effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end effector 112. In exemplary embodiments, at least one tracking marker 118 of the plurality of tracking markers 118 can be mounted or otherwise secured to the end effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end effector 112, the patient 210, and the surgical tools 608) to be tracked by the robot 102. In exemplary embodiments, system 100 can use tracking information collected from each of the marked objects to calculate the orientation and location, for example, of the end effector 112, the surgical instrument 608 (e.g., positioned in the tube 114 of the end effector 112), and the relative position of the patient 210.

In exemplary embodiments, one or more of markers 118 may be optical markers. In some embodiments, the positioning of one or more tracking markers 118 on end effector 112 can maximize the accuracy of the positional measurements by serving to check or verify the position of end effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
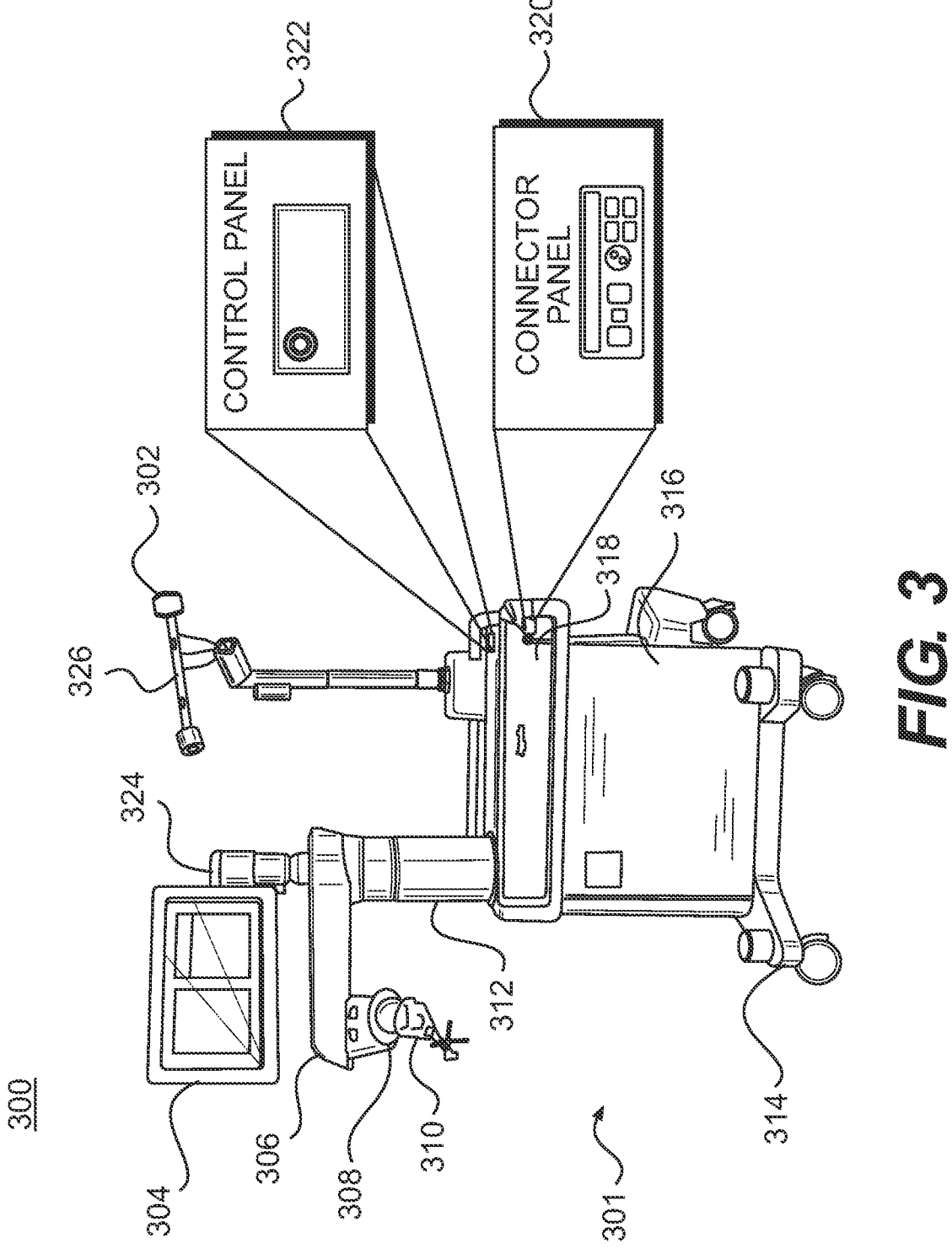
FIG. 3 illustrates a surgical robotic system in accordance with an exemplary embodiment.
Figure 4:
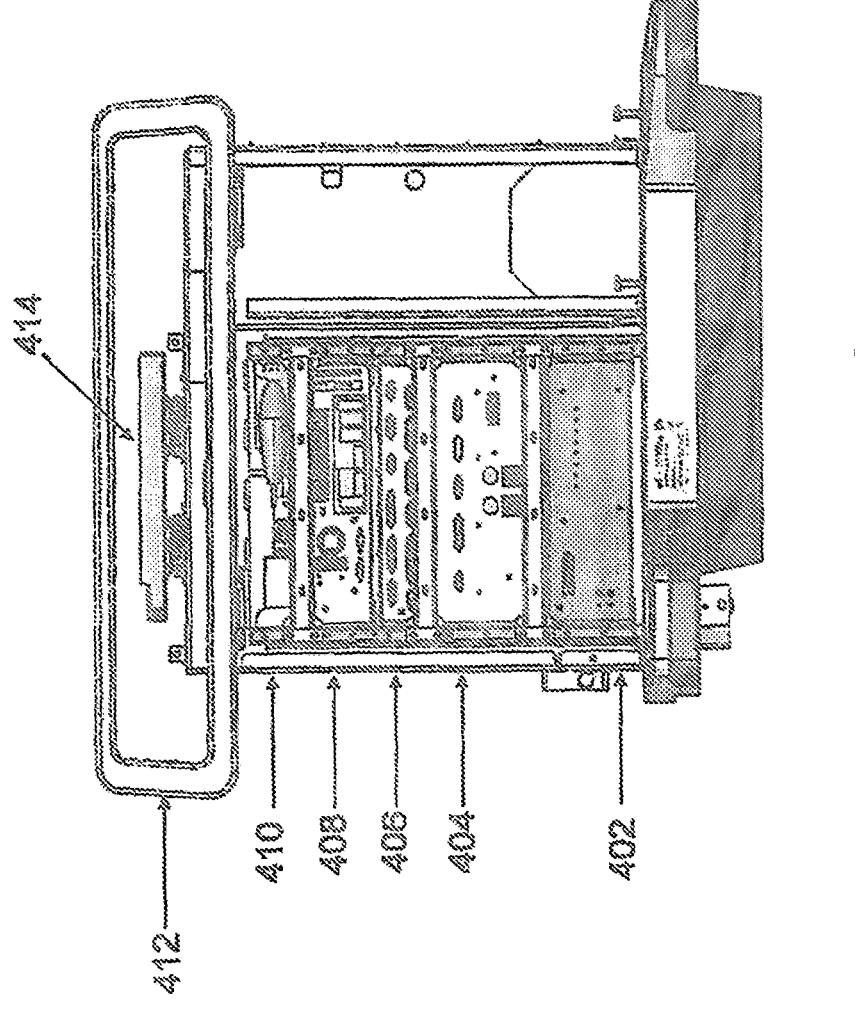
FIG. 4 illustrates a portion of a surgical robot in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2. FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
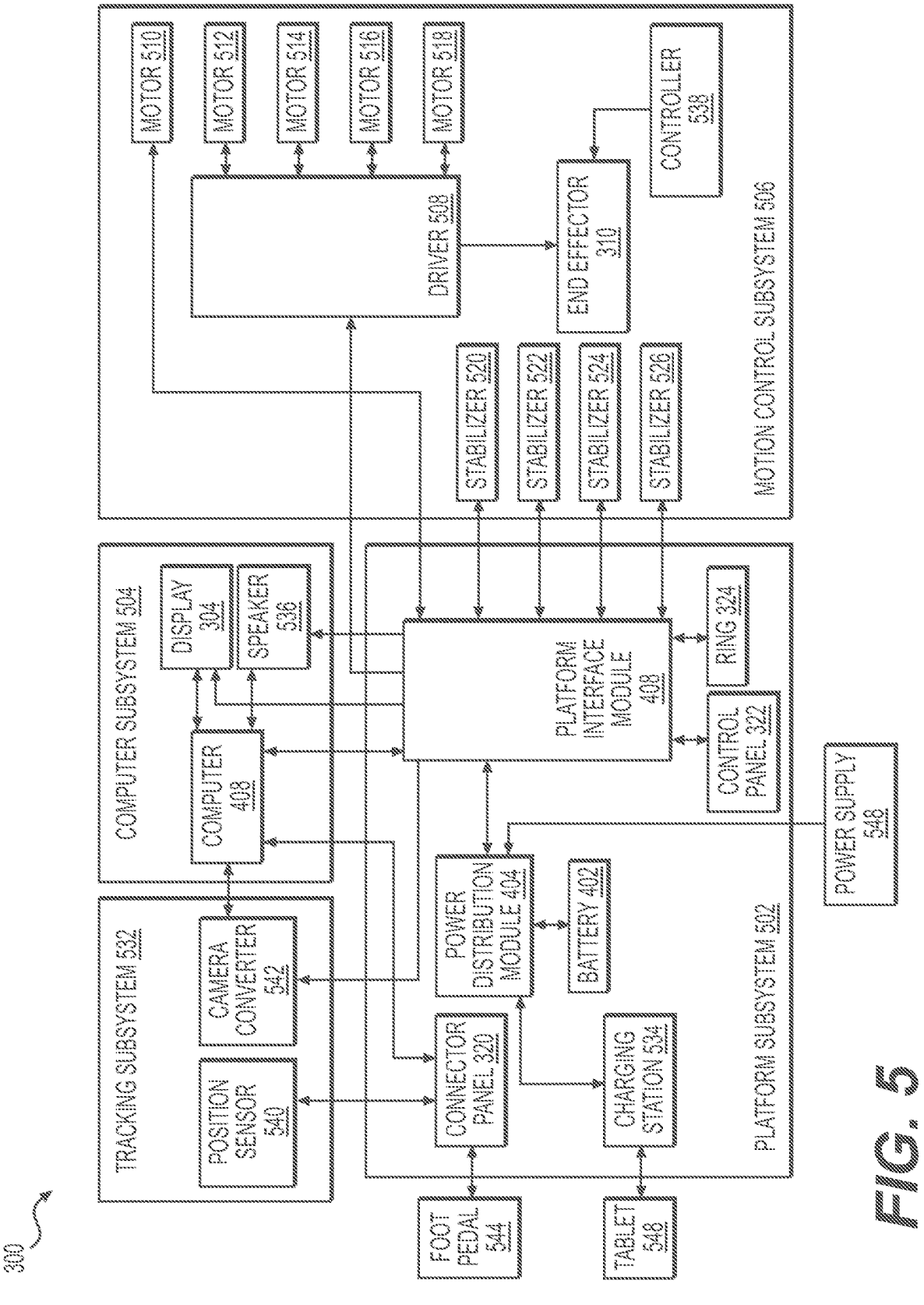
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein. Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure. Motion control subsystem 506 may be configured to physically move vertical column 312, upper arm 306, lower arm 308, or rotate end effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end effector 310 in a manner such that one may control the roll and one may control the tilt, thereby providing multiple angles that end effector 310 may be moved. These movements may be achieved by controller 538 which may control these movements through load cells disposed on end effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
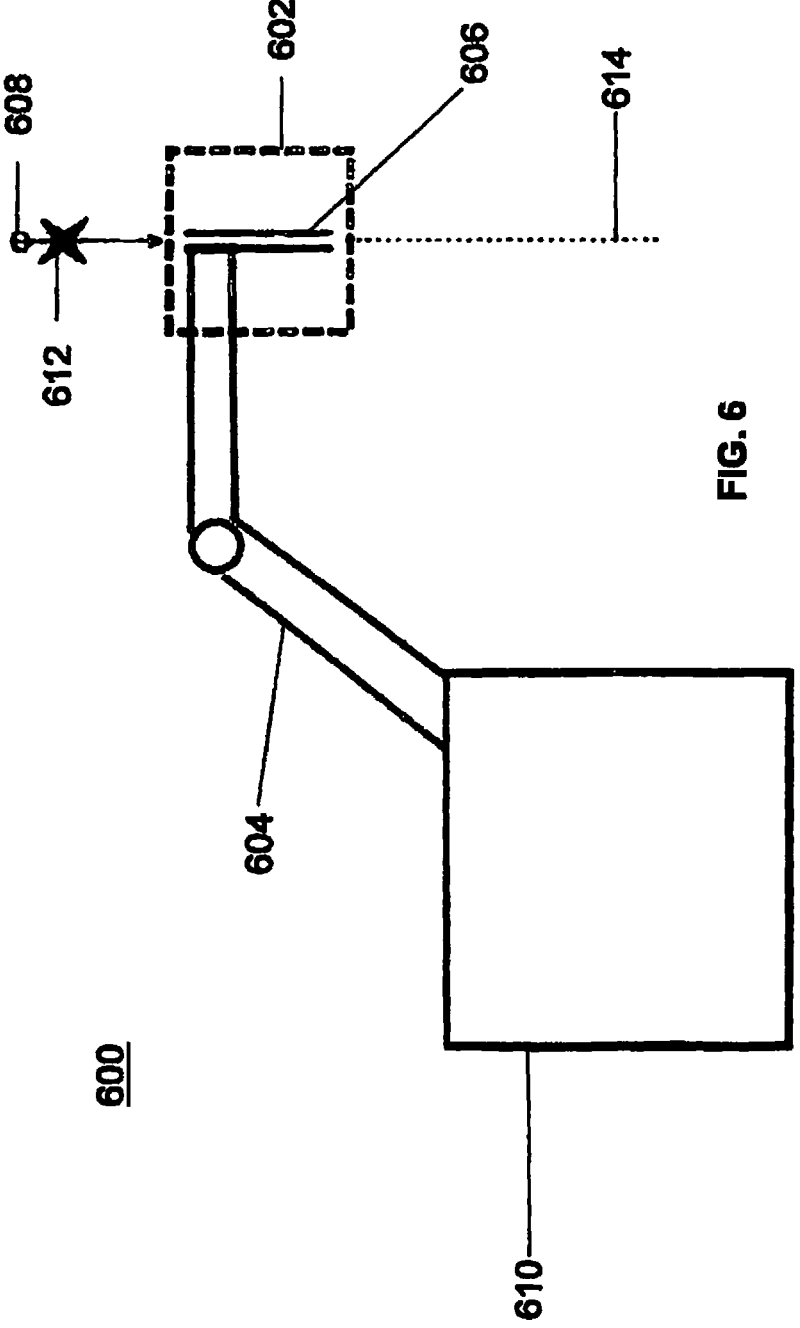
FIG. 6 illustrates a surgical robot in accordance with an exemplary embodiment.

FIG. 6 illustrates a surgical robot system 600 consistent with an exemplary embodiment. Surgical robot system 600 may comprise end effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end effector 602 so that surgical robot system 600 may assist a user (for example, a surgeon) in operating on the patient 210. Surgical robot system 600 may be consistent with previously described surgical robot system 100 and 300.

Figure 8:
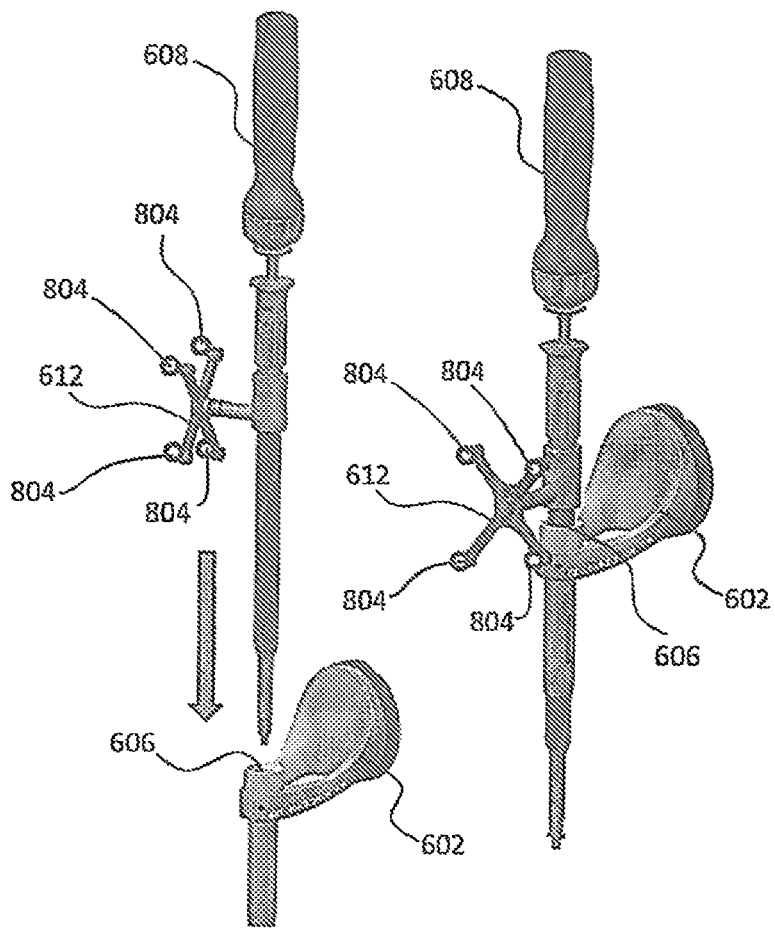
FIG. 8 illustrates a surgical instrument and the end effector, before and after, inserting the surgical instrument into the guide tube of the end effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end effector 602, and/or the patient 210. The tracking devices may be consistent with those structures described in connection with camera stand 302 and tracking subsystem 532.

Figures 7A, 7B, 7C:
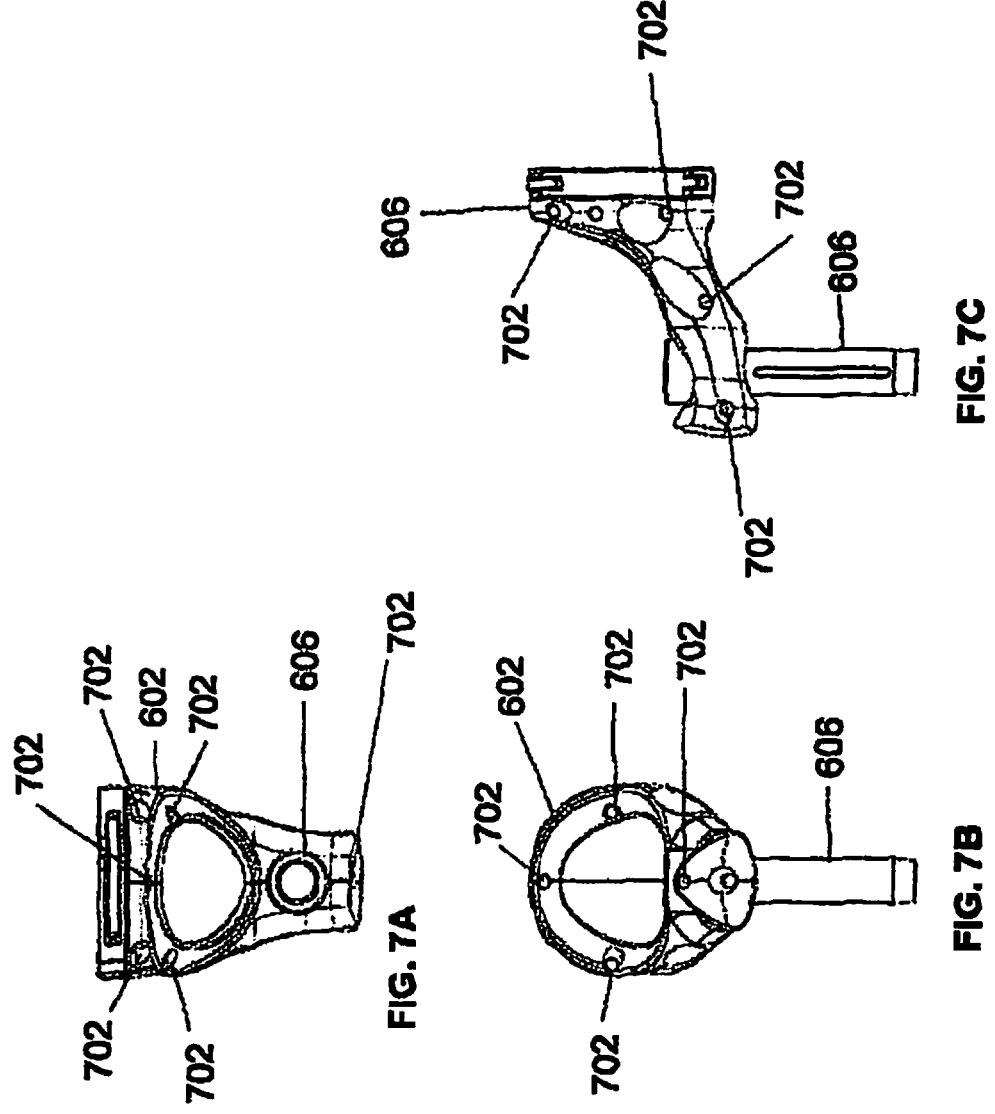
FIGS. 7A-7C illustrate an end effector in accordance with an exemplary embodiment.

FIGS. 7A, 7B, and 7C illustrate a top view, front view, and side view, respectively, of end effector 602 consistent with an exemplary embodiment. End effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end effector 602 may be controlled by the system 100, 300, 600, and when the markers 702 are deactivated, the end effector 602 may be locked in position and unable to be moved by the system 100, 300, 600.

Markers 702 may be disposed on or within end effector 602 in a manner such that the markers 702 are visible by one or more cameras 200, 326 or other tracking devices associated with the surgical robot system 100, 300, 600. The camera 200, 326 or other tracking devices may track end effector 602 as it moves to different positions and viewing angles by following the movement of tracking markers 702. The location of markers 702 and/or end effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end effector 602 is in a desirable position in relation to robot arm 604, robot base 610, the patient 210, and/or the user.

For example, as shown in FIG. 7A, markers 702 may be placed around the surface of end effector 602 so that a tracking device placed away from the surgical field 208 and facing toward the robot 102, 301 and the camera 200, 326 is able to view at least 3 of the markers 702 through a range of common orientations of the end effector 602 relative to the tracking device 100, 300, 600. For example, distribution of markers 702 in this way allows end effector 602 to be monitored by the tracking devices when end effector 602 is translated and rotated in the surgical field 208.

In addition, in exemplary embodiments, end effector 602 may be equipped with infrared (IR) receivers that can detect when an external camera 200, 326 is getting ready to read markers 702. Upon this detection, end effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end effector 602 and adjust the instrument 608 is evident in FIG. 8. The hollow tube or guide tube 114, 606 of the end effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figures 9A, 9B, 9C:
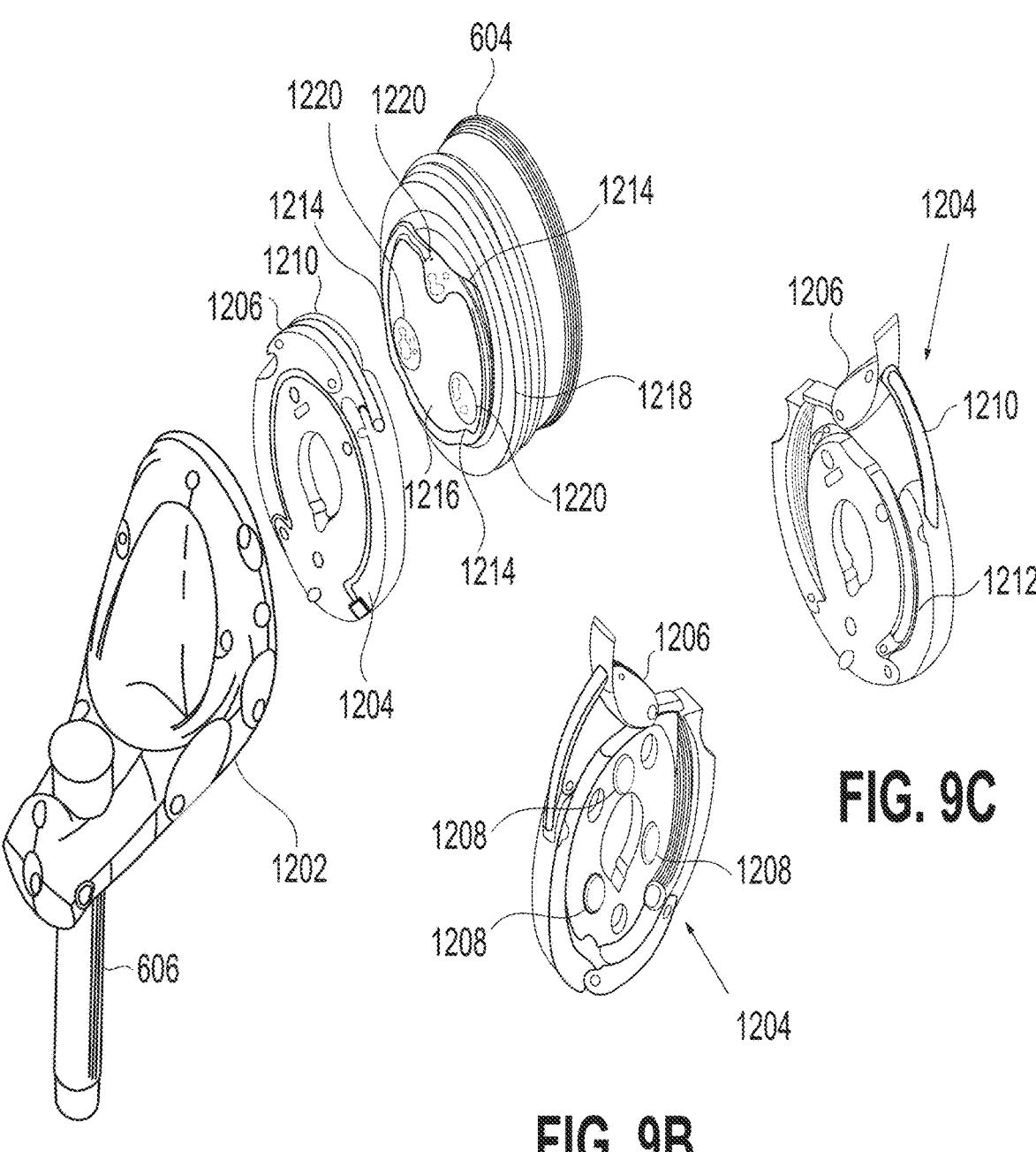
FIGS. 9A-9C illustrate portions of an end effector and robot arm in accordance with an exemplary embodiment.

FIGS. 9A-9C illustrate end effector 602 and a portion of robot arm 604 consistent with an exemplary embodiment. End effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220. [0072] End effector 602 may mechanically interface and/or engage with the surgical robot system and robot arm 604 through one or more couplings. For example, end effector 602 may engage with robot arm 604 through a locating coupling and/or a reinforcing coupling. Through these couplings, end effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end effector 602 regardless of the orientation of end effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end effector 602 to robot arm 604 as lip 1212 and lip 1218 engage clamp 1204 in a manner to secure end effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end effector 602 may be robustly secured to robot arm 604.

Spring 1210 may be a curved beam in tension. Spring 1210 may be comprised of a material that exhibits high stiffness and high yield strain such as virgin PEEK (poly-ether-ether-ketone). The linkage between end effector 602 and robot arm 604 may provide for a sterile barrier between end effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end effector 602 and/or robot arm 604 that slips over an interface between end effector 602 and robot arm 604 and tightens with a screw mechanism, an over center linkage, or a cam mechanism.

Figure 10:
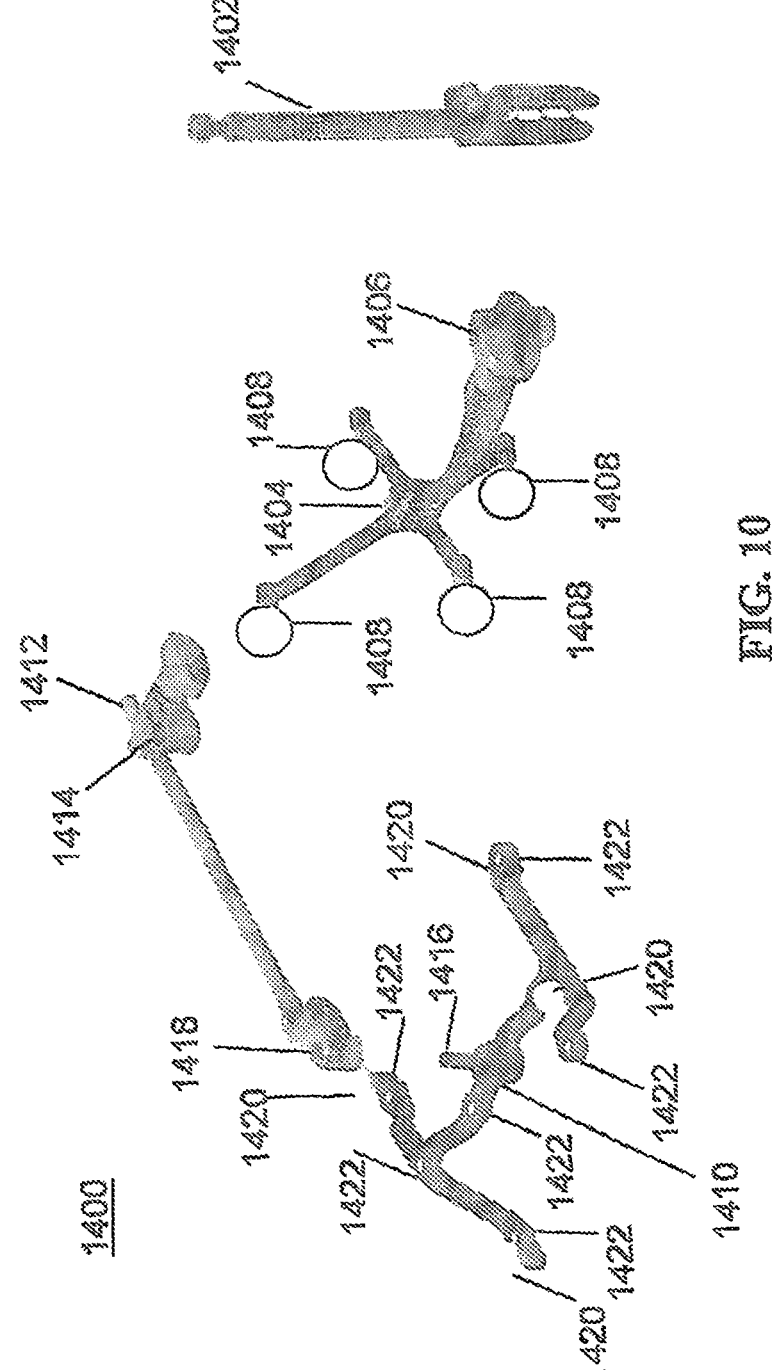
FIG. 10 illustrates a dynamic reference array, an imaging array, and other components in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
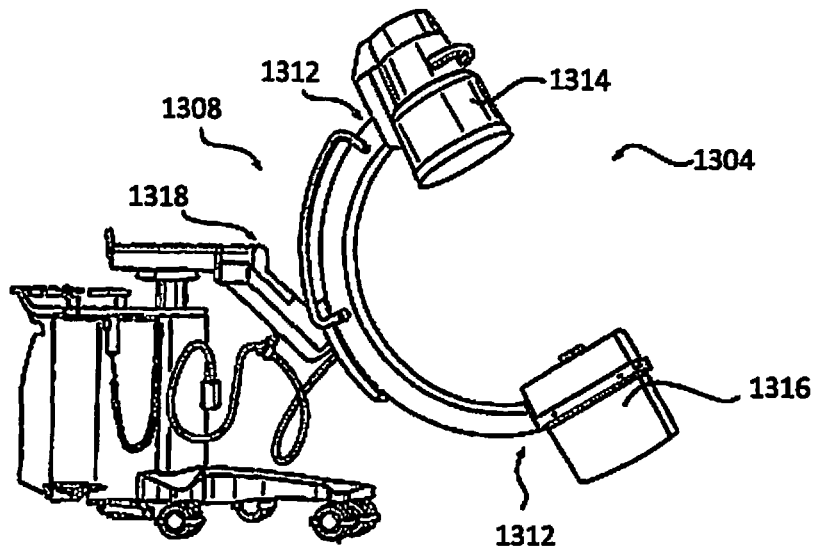
FIG. 12A-12B illustrate embodiments of imaging devices according to exemplary embodiments.
Figure 12B:
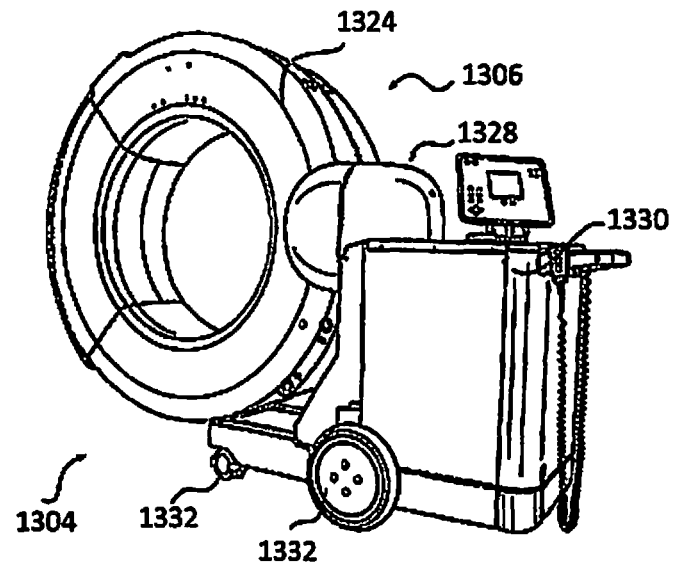

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Figure 13:
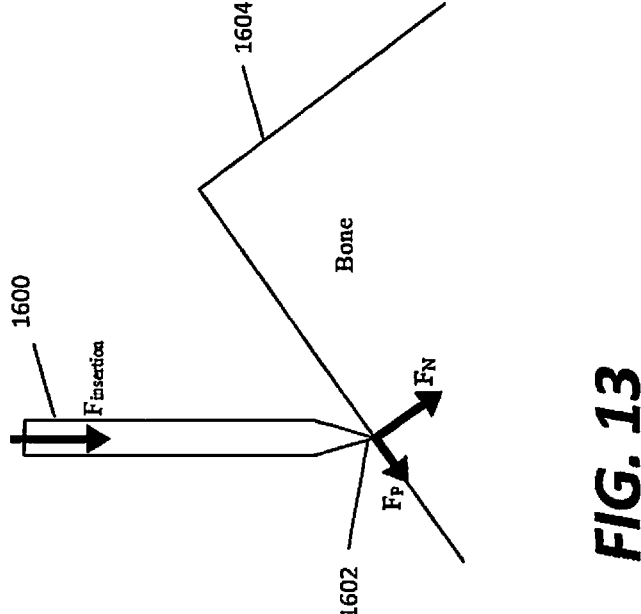
FIG. 13 illustrates certain forces applied to a target bone from a surgical tool.

Referring now to FIG. 13 of the present disclosure, FIG. 13 illustrates surgical tool 1600 with tip 1602 and bone 1604, which may be target bone of a patient during a surgical procedure. Also illustrated are three forces ($F_{insertion}$, $F_p$, and $F_n$) associated with tool 1600 as it penetrates bone 1604, for example during a medical procedure where a surgeon drills into a patient's bone. Surgical tool 1600 may be any surgical instrument or tool associated with surgical applications including but not limited to a drill, an awl, a tap, a screwdriver, or other types of surgical tools. These forces may be referred to as reactive forces at the tool-bone interface when a force intended to penetrate bone is applied to a tool. The force of insertion ($F_{insertion}$) can be resolved into a component force normal to the surface ($F_N$) and a component force parallel to the surface ($F_P$).

While tip 1602 of instrument 1600 is disposed and poised at the surface of bone 1604, physical mechanisms resulting from the aforementioned forces include the following: (1) bone 1604 may move away from the insertion force ($F_{insertion}$) en masse, (2) frictional resistance preventing slippage of tip 1602 may be overcome resulting in tip 1602 to travel laterally in direction parallel to bone surface 1604 in the direction of $F_p$, or (3) the tip may penetrate the bone in an intended direction such as $F_{insertion}$.

The present disclosure seeks to keep instrument 1600 aligned where desired and prevent tip 1602 from wandering or "skiving" due to the force parallel ($F_p$) to the surface of bone 1604. Instrument 1600 may be operated through a rigidly held guide tube with close tolerance between the tube's inner diameter and the tool's outer diameter. Such guide tube has been described previously herein. In order for the guide tube to be completely effective in driving instrument 1600 or another piece of hardware into bone 1604, the tube should not move relative to bone 1604 and instrument 1600 or other hardware should not bend relative to the tube or bone 1604.

As previously described herein, a surgical robot capable of being rigidly locked to the floor can be effective in maintaining a stationary, rigid position of a guide tube (for example, robot system 300). Skiving may result in multiple scenarios in the context of robot-assisted surgery. For example, during insertion of instrument 1600 at an angle through the guide tube and into contact with bone 1604, the force generated parallel to the surface of bone 1604, which may depend, at least in part or in total, on the instrument insertion force and insertion angle, may lead to bending of the instrument and/or movement of the patient.

As another example, inserting instrument 1600 through a guide tube, either at an angle to bone 1604 or perpendicular to bone 1604, may result in instrument 1600 reaching a depth or point where instrument 1600 is fully within the guide tube or the instrument's handle bottoms out (i.e., is fully on the top entry of the guide tube, at which point the tool can no longer be inserted any further unless the tube is advanced longitudinally). If a surgeon applies additional downward force after instrument 1600 is bottomed out, that force is absorbed by the guide tube, not transferred to instrument 1600 for further penetrating bone 1604. This example may lead to several unintended results. One unintended result may be that if the surgeon does not realize that instrument 1600 is bottomed out, addition force may damage or strip the screw hole in the patient bone by rotating a screwdriver or tap while screw or tap cannot move forward. Another unintended result may be that the surgeon may not achieve the desired or expected penetration of the instrument or tool that the surgeon is attempting to advance.

As previously described, robot system 300 may include load cells (which control multiaxial movement of the robot arm) disposed on end effector 310. Using a multi-axis load cell mounted to the guide tube and/or end effector, one may quantify the lateral deflection and longitudinal bottoming out forces/torques described above in real time during surgery. Consistent with the present disclosure, robot system 300 may use the forces and moments monitored by a multi-axis load cell on the robot's guide tube to provide specific feedback to the surgeon to help prevent the instrument or tool from being inserted inaccurately, incompletely or poorly.

Figure 14:
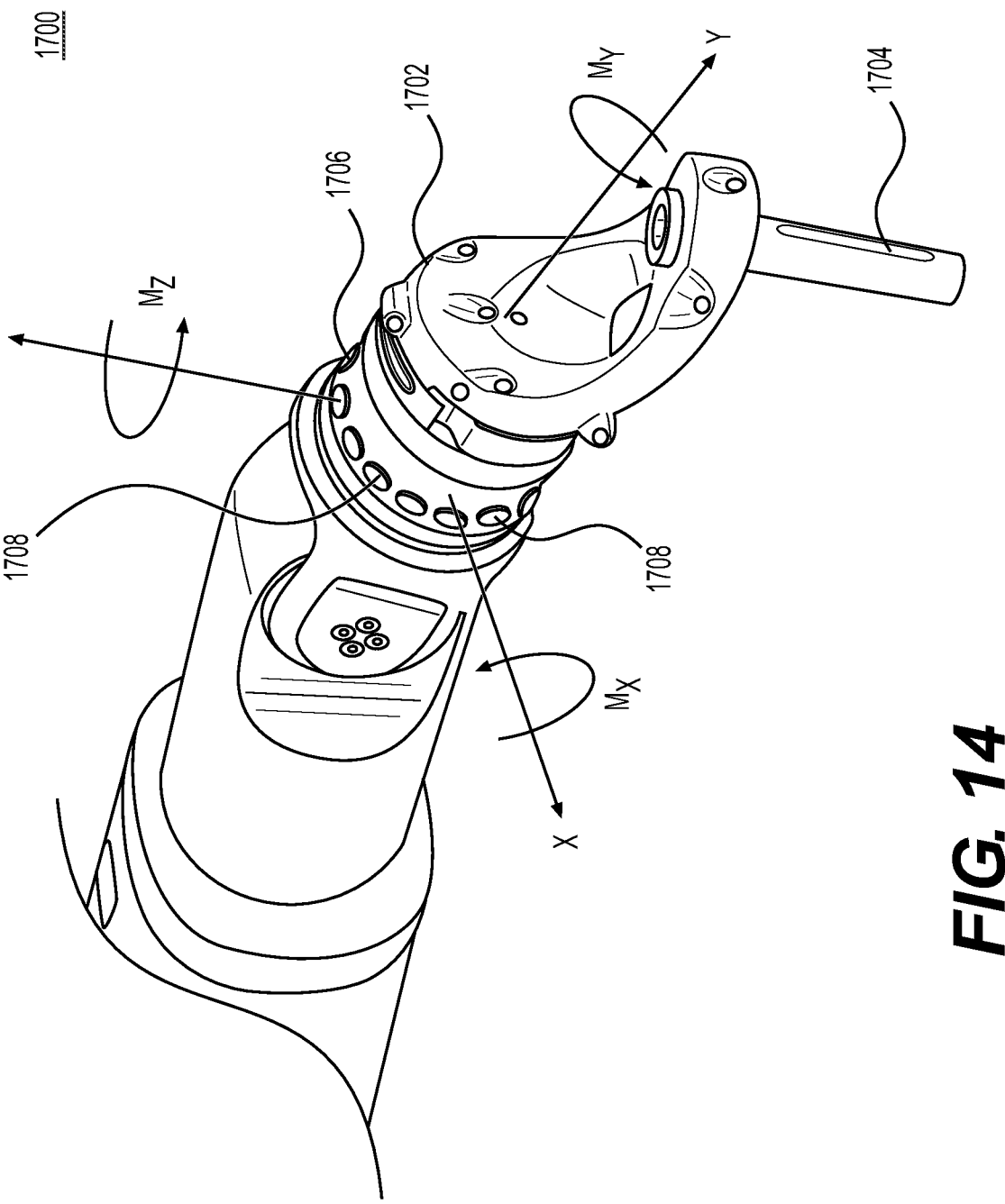
FIG. 14 illustrates an end-effector of a robot system consistent with the principles of the present disclosure.

FIG. 14 illustrates an exemplary embodiment of a robot arm 1700 consistent with the present disclosure. Robot arm 1700 may include end-effector 1702, guide tube 1704, and bracelet 1706 mounted to end-effector 1702. Bracelet 1706 may further include one or more multi-axis load cells 1708.

Multi-axis load cell 1708 mounted to end effector 1702 via bracelet 1706 may be capable of providing measurements of torques and forces along, about, and across an axis of the guide tube (for example, a longitudinal axis of guide tube 1704). Multi-axis load cells 1708 may comprise strain gauges applied across appropriately oriented rigid internal members such that they may accurately measure forces and torques while elastically deforming by a negligible amount.

Multi-axis load cell 1708 may support end-effector 1702 and guide tube 1704 in a manner such that the forces and moments applied to guide tube 1704 may be detected by one or more of load cells 1708. As shown in FIG. 14, directions of forces and moments sensed by the one or more load cells 1708 are depicted with arrows Mx, My, and Mz and arrows labeled X, Y, and Z.

In a case where a surgeon is inserting instrument 1600 (for example, a drill) through guide tube 1704 and penetrating bone 1604 with instrument 1600 at a position normal to a flat surface, the majority of the force applied by the surgeon may be transferred to the drill as longitudinal force down the axis of the drill bit. It may be that a relatively small lateral force (in the X or Y direction as shown in FIG. 14) or torque across the axis of the guide tube (Mx or My as shown in FIG. 14) would be expected, and a relatively small longitudinal force applied to guide tube 1704 would be expected (for example in the Z direction as shown in FIG. 14).

Continuing with the last example, as the surgeon torques the tool, a relatively small amount of that torque should be transferred to the load cell (shown as Mz in FIG. 14) since the tool should rotate freely inside guide tube 1704. It may be possible that the surgeon may misalign the applied force, in which case the rigidly held guide tube 1704 may act to prevent the tool from moving laterally. This lateral force may be monitored by one or more of the multi-axis load cells 1708 as a moderate lateral (X, Y or combined XY) force.

In cases where instrument 1600 (e.g., a drill or tool) is inserted under conditions where instrument 1600 strikes bone 1604 at a steep angle causing tip 1602 to skive, the forces detected by one or more multi-axis load cells 1708 may change in certain predictable ways. For example, the moment across guide tube 1704 (Mx or My as shown in FIG. 14) may increase and the force lateral to guide tube 1704 (X or Y direction in FIG. 14) may increase. The X-Y orientation of this increased moment may be perpendicular to the direction of slope of bone 1604 as shown in FIG. 13. Similarly, the orientation of the force would be in the direction of the downhill slope of bone 1604, as shown in FIG. 13, and perpendicular to the increased moment. Due to the lateral force that may instrument 1600 to press against the side of guide tube 1704 and slightly bend, a slightly increased downward force on guide tube 1704 (Z direction as shown in FIG. 14) may be expected. In this example, it may be that the prominent increased values should be in this bending moment and lateral force.

In another example, in cases where instrument 1600 (for example, a drill or tool) bottoms out within guide tube 1704, a sudden spike in the downward longitudinal force in the direction of guide tube 1704 (Z direction shown in FIG. 14) may be expected without any substantial increase in any other detected moment or force as the surgeon applies additional downward force. Additionally, if the surgeon were to release instrument 1600, some residual downward force (Z) may be expected since instrument 1600 may still interact with guide tube 1704. For example, if the surgeon were inserting a screw using a locking screwdriver but the screwdriver bottomed out, after releasing the screwdriver, its handle under tension against the top of the guide tube would cause a downward force to remain.

The robot system via software may continuously monitor forces and moments and check whether each force and moment remains within the normal expected range or threshold. Software could react with messaging when a force/moment pattern that meets the above expected undesirable conditions is encountered. Examples of messages could be "caution—possible skiving of the tool may be occurring" or "caution—the tool may have reached its depth stop".

Figure 15:
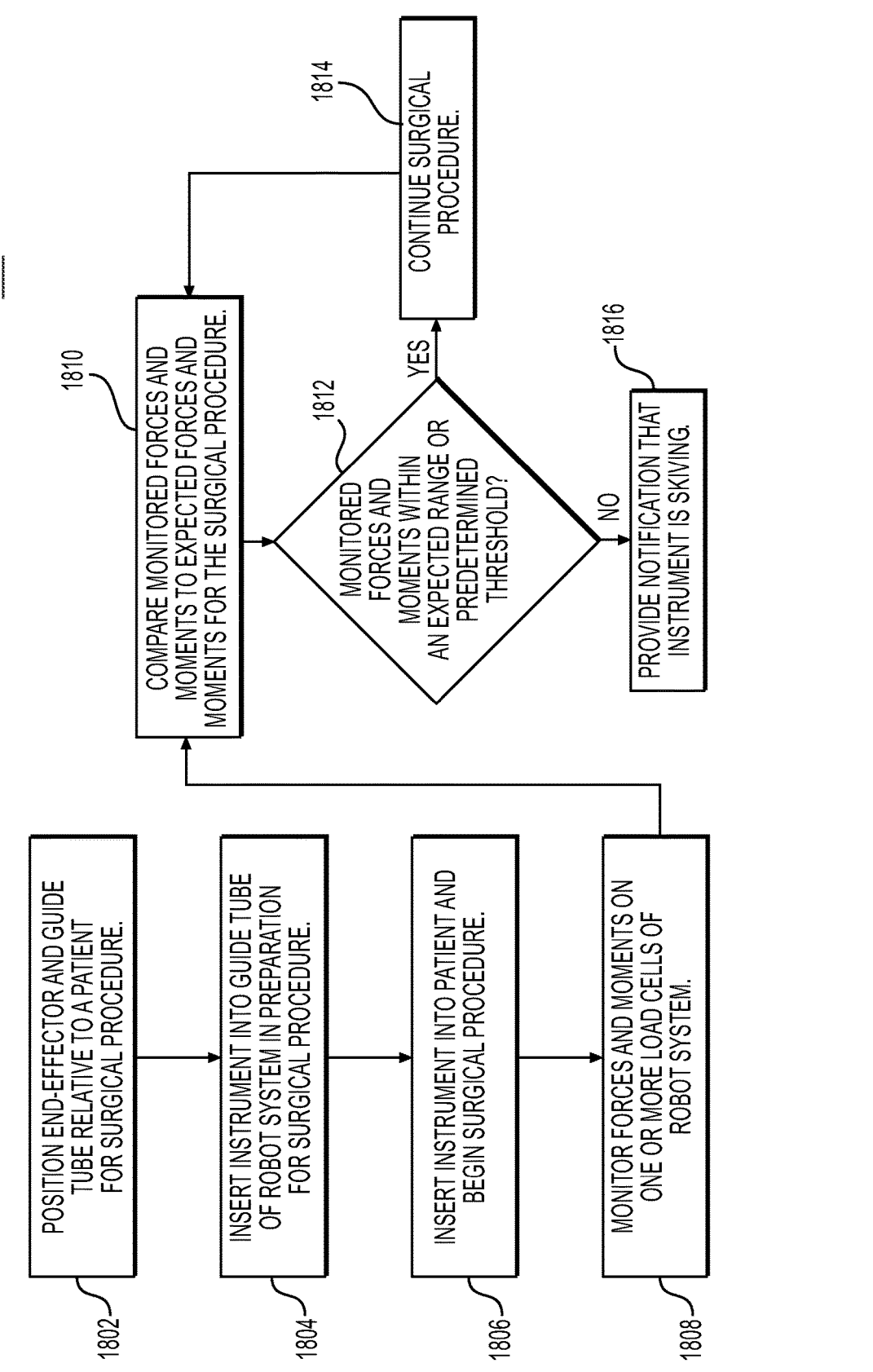
FIG. 15 illustrates an exemplary method for detecting unexpected movement of a surgical instrument consistent with the present disclosure.

FIG. 15 illustrates and an exemplary method 1800 for detecting the presence of skiving of an instrument during a surgical procedure. Method 1800 begins at step 1802 where, as previously discussed herein, the end-effector and guide may be automatically or manually positioned to a location relative to a patient undergoing a surgical procedure. At step 1804, an instrument or tool (for example, instrument 1600) may be inserted into the guide tube of the robot system. At step 1806, the instrument may be inserted into the patient and advanced to contact a target bone of the patient for the surgical procedure. For example, instrument may be advanced to contact the target bone in order to drill screw holes for pedicle screws, as previously described. At step 1808, robot system may monitor the forces and moments measured by one or more load cells present on the robot system, for example, disposed on the end-effector. At step 1810 the monitored forces and moments may be compared against the expected forces and moments that would be consistent with the surgical procedure. At step 1812, if the monitored forces and moments fall within an expected range or predetermined threshold, the surgical procedure is continued at step 1814 and method 1800 continues to step 1810 as previously described. If the monitored forces and moments do not fall within an expected range or predetermined threshold, an alert or notification is provided by the robot system to indicate the presence of skiving.

In another embodiment, there is provided a method to quantify the number of millimeters of skiving that occurs and a method to overcome any skiving that does occur.

As described above, a 6-axis load cell mounted to a robot arm is configured to detect forces that are oriented laterally relative to a guide tube. In an optimal procedure, the lateral forces are applied on the guide tube should generally be minimal. The main force detected and applied in one embodiment should be along the axis of the guide tube. In embodiments, where there are lateral forces that occur, these forces can cause skiving or movement of a surgical instrument along a bone surface without penetrating bone, or if the forces excessive lateral skiving or movement of the bone away from the surgical instrument. In some embodiments, lateral forces may cause the tip of the tool, to bend and deflect laterally away from the central axis of the surgical instrument shaft and guide tube.

In certain embodiments, a robotic arm may hold the guide tube in an immobile position even in the presence of lateral forces. As lateral forces push on bone and cause the bone to move away from the rigid guide tube, in one embodiment, the amount of bone movement that occurs can be tracked with a DRB (dynamic reference base) attached to the patient. The DRB comprises an array of tracking markers such as reflective spheres, the positions of which are tracked using a tracking system such as the Polaris Spectra optical tracking system (Northern Digital, Inc.) Since the amount of bone movement is monitored, any offset can be reported by the system to the user, and automatic robotic adjustment of the guide tube position can offset additional movement caused by the lateral forces.

Figure 16:
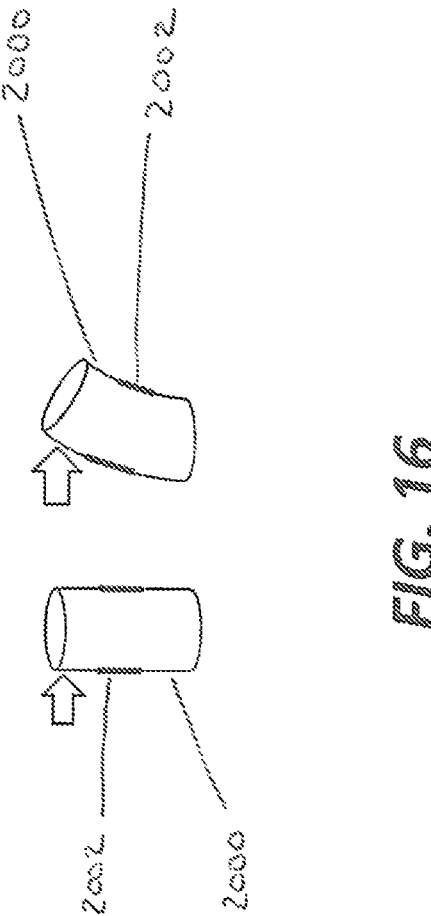
FIG. 16 illustrates an exemplary method for detecting deflection of a surgical instrument.

Now turning to FIG. 16, in some embodiments, if the instrument tip bends relative to the instrument's tracking array as a result of lateral forces, the amount of deflection of the instrument relative to its tracking array may be measured. In one embodiment, strain gauges may be used to measure the instrument tip deflection caused by lateral forces. Strain gauges are typically resistance-based and are configured to detect slight increases or decreases in length of a surface. In one embodiment, a pair of strain gauges oriented parallel, along the axis of the instrument, and attached to the surface of the instrument on opposite sides of the shaft may measure the deflection toward or away from either strain gauge. In another embodiment, three or more gauges may be mounted in parallel around the perimeter of the instrument at a given longitudinal position and configured to provide estimates of the magnitude of longitudinal shortening or lengthening around the perimeter of an instrument at the location where the strain gauges are attached.

FIG. 16 illustrates an exaggerated lateral deflection of an instrument 2000 due to lateral forces, indicated by the arrow. Strain gauges 2002 mounted on opposing sides of the instrument 2000 measure the elongation of the instrument 2000 on the side the force is measured and shortening of the instrument 200 on the side opposite to the force. If an instrument 2000 or guide tube is deflected, the side of the shaft toward which it is deflected decreases in length and the opposite side of the shaft increases in length. The deflection of cylinders, which comprise the shaft of an instrument or guide tube, utilizes the following equations in response to applied lateral forces: deflection=$FL^3/3EI$ where F is the applied lateral force at the tip; L is the length from tip to the fulcrum (assumed to be cantilevered); E is the modulus of elasticity of the shaft material, such as cobalt chrome or stainless steel; I is the moment of inertia, which is a geometric property related to the cross section of the tool. In one embodiment, when the instrument is configured as a cylinder, I=$\Box d^4/64$, where d is the diameter of the cylinder.

If the instrument is a uniform cylinder, the tip deflection can be estimated by knowing the lateral force and the contact points of the instrument in the guide tube. In some embodiments if the instrument is tapered toward the tip or is otherwise non-uniform, the exact point of contact within the guide tube may be difficult to determine since it would be within the tube at the point where the instrument starts tapering and is no longer in tight contact with the tube. In this case calibrating the tip deflection is based on the strain gauges mounted to the instrument, specifically the attachment points of the strain gauges, and the geometry of the internal portion of the guide tube. This data is then used to calculate the estimated deflection of the instrument 2000.

In another embodiment for calibrating the tip deflection, strain measurements from a set of strain gauges attached around the shaft of the instrument may be used with a neural network. A neural network is a mathematical method in which patterns of responses of nodes (in this case, the output from the array of strain gauges) are used as inputs to produce well-defined outputs (in this case, lateral deflection) if the outputs are distinctive enough for different sets of inputs. In some embodiments, the neural network for instrument deflection measurement is used by applying known test loads laterally at different approach angles and contact locations around the tool tip while measuring deflection using optical tracking, coordinate measurement machine (CMM) or other means. Once this data is a part of the neural network, the output of the strain gauges would be fed continuously into the neural network computer model and deflection data may be streamed out and displayed by the system.

Figure 17:
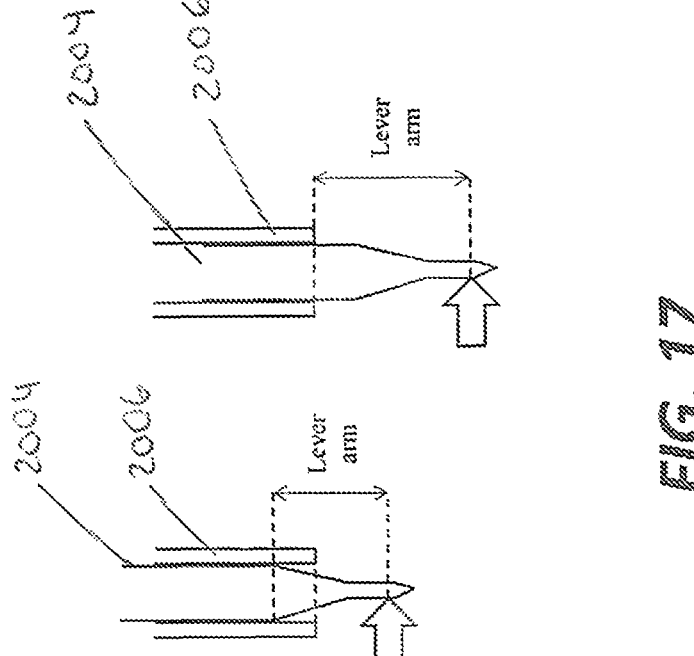
FIG. 17 illustrates a two-stem method for detecting deflection of an instrument with respect to a guide tube.

In another embodiment, a neural network or physical modeling may be used by applying data from the instrument 2004 and guide tube 2006 interaction in two zones, as illustrated in FIG. 17. In the first zone, the instrument's 2004 taper ends within the guide tube 2006 and so a lever arm for deflection is the point of application of force to the point where the largest diameter of the instrument touches the guide tube. The lever arm remains fixed for a fixed point of load application as long as the instrument 2004 remains in this zone. In the second zone, the instrument's 2004 taper ends outside the guide tube 2006 and so the lever arm for deflection is the point of application of force to the point where the instrument 2004 exits the guide tube 2006. The lever arm continuously increases as more of the instrument 2004 protrudes. Based on the instrument's tracking array location relative to the guide tube's tracking array location, the system can keep track of the current zone and appropriately interpret the neural network model or physical model of the tool to calculate tip force and displacement.

Figure 18:
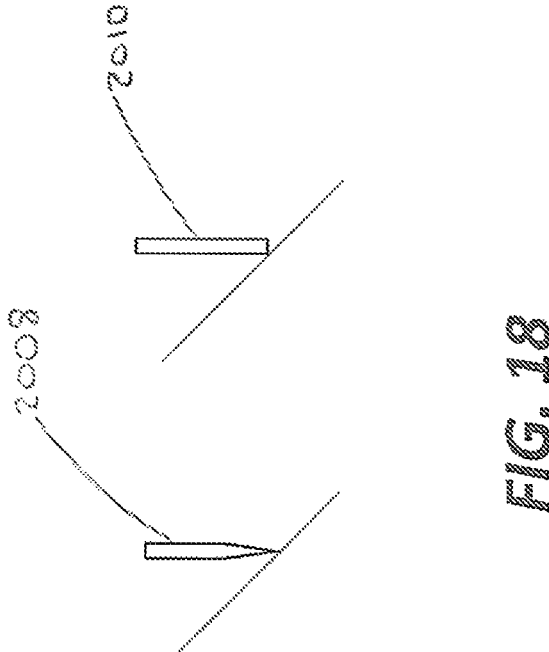
FIG. 18 illustrates a comparison of an instrument with axial cutting capabilities vs. an instrument with axial and lateral cutting capabilities.

In one embodiment, a 6-axis load cell mounted to a robot arm can assess forces and moments caused by the interaction of the tip of the instrument with a bone. If skiving occurs due to lateral forces being applied to the instrument, the following method may be utilized to overcome or mitigate any skiving that may occur. In one embodiment, the instrument tip can be configured to be sharp and capable of penetrating the bone with axial cutting capabilities as well as side-cutting capabilities. The sharpened tip of the instrument when lateral forces are applied may be similar to drilling a surface at a 45° angle relative to the drill as shown in FIG. 18. Specifically, FIG. 18 illustrates an instrument 2008 having axial cutting capabilities and instrument 2010 illustrates an axial and lateral side-cutting capabilities striking an inclined surface.

Figure 19:
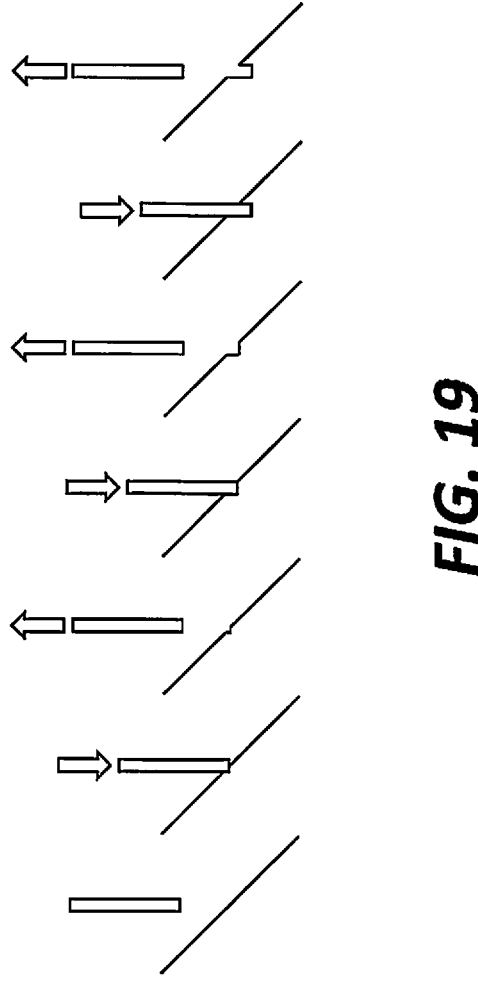
FIG. 19 illustrates a method for insertion of an instrument through an angulated surface.

In the preferred embodiment, an instrument with a sharpened tip will cut through the surface of bone before skiving. In some cases, even if the instrument is provided with a greater cutting surface, skiving may still be possible. In these cases, in one embodiment, a repetitive puncturing action may be used to insert the instrument through the surface of the bone without moving the bone. This tapping motion may be applied by a surgeon, and a tactile response to the penetration is signaled when the instrument has advanced through the surface of the bone as illustrated in FIG. 19. The stepwise or tapping motion as shown in FIG. 19, prevents skiving from occurring.

Figures 20A, 20B, 20C, 20D, 20E:
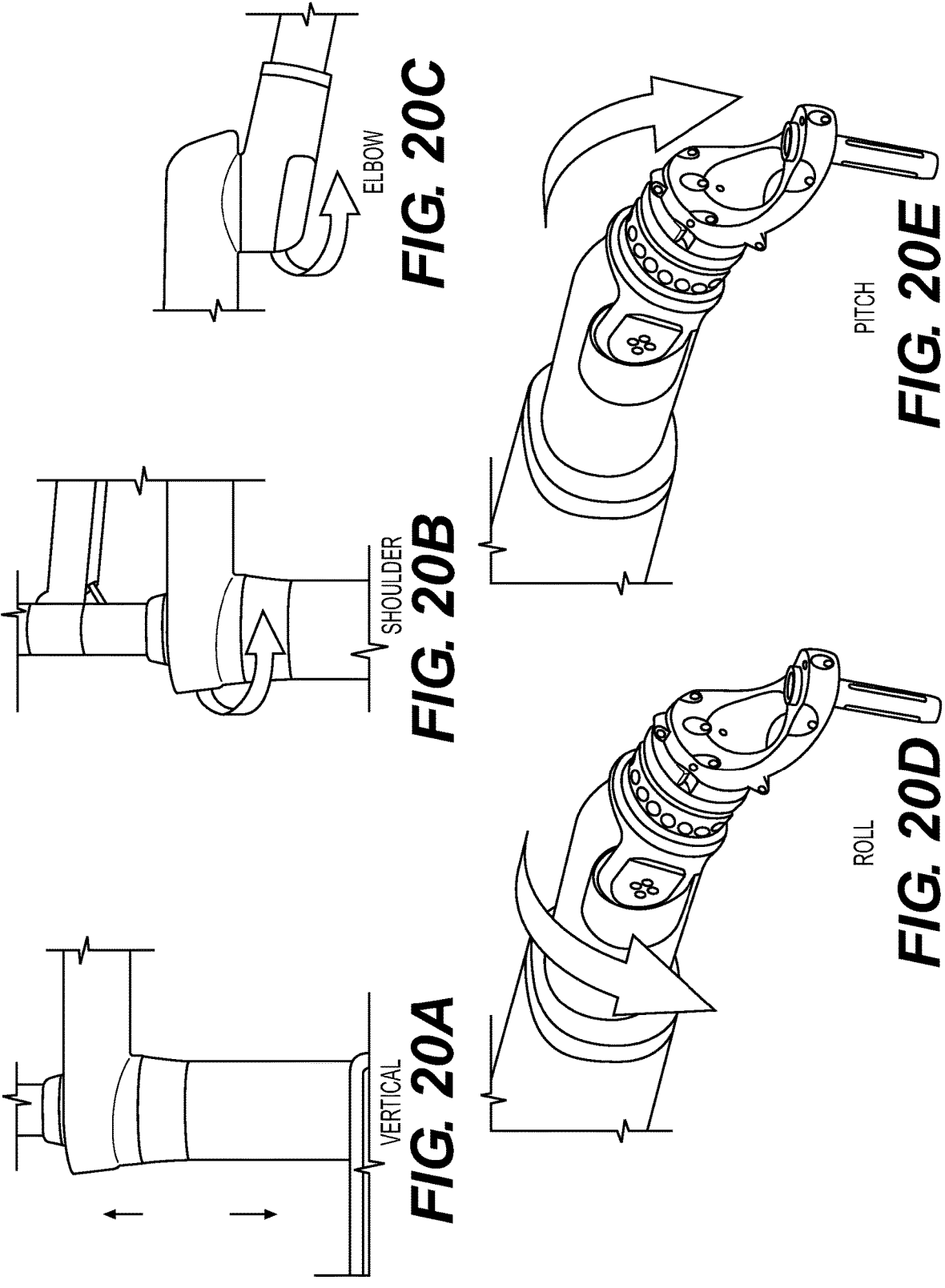
FIGS. 20A-E illustrate five degrees of freedom associated with a robotic surgical system.

Turning now to FIGS. 20A-E, a robotic surgical system having five degrees of freedom is illustrated. These five degrees of freedom from base of the robotic surgical system to the end effector include: (1) vertical linear motion (FIG. 20A), (2) shoulder rotation in the horizontal plane (FIG. 20B), (3) elbow rotation in the horizontal plane (FIG. 20C), (4) roll of the forearm (FIG. 20D), and (5) pitch of the end effector (FIG. 20E). With these five degrees of freedom, it is possible to move the robotic surgical system into a range of positions and angles where it can hold a guide tube to facilitate placement of screws and other straight line trajectories into the body.

These five degrees of freedom allow the guide tube of the end effector to be aligned with a trajectory vector, but the rotational position of the guide tube about the trajectory vector may not be independently selected and is dependent on the positions of these other joints. When using five degrees of freedom in this configuration, the movement of the robot along a straight line approaching the patient is usually associated with some residual rotation of the guide tube during the movement (FIGS. 21A-C).

Figures 21A, 21B, 21C:
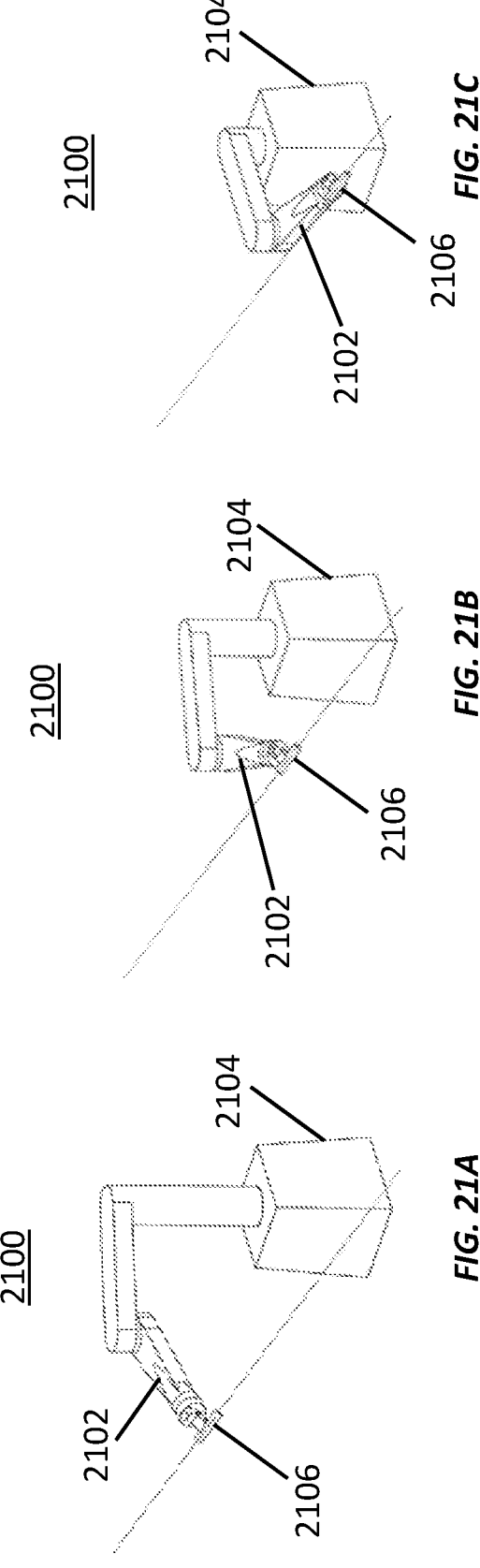
FIGS. 21A-C illustrates a robotic surgical system consistent with the principles of the present disclosure.

FIGS. 21A-C illustrate a robotic surgical system 2100, including robot arm 2102, base 2104, and guide tube 2106. Together, FIGS. 21A-C show movement of robot arm 2102 along a straight line. As coordinated movement of the joints illustrated in FIGS. 20A-E occurs, constraining motion to keep guide tube 2106 centered along the line, the rotational position of guide tube 2106 relative to the line and the room varies.

Figure 23:
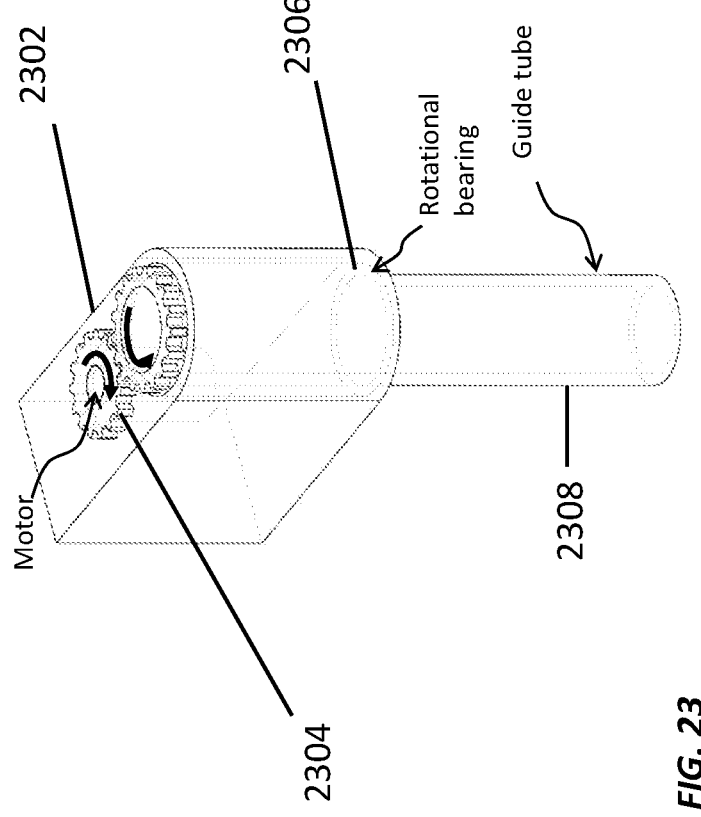
FIGS. 23-25 illustrate a portion of the robotic surgical system consistent with the principles of the present disclosure.

According to principles of the present disclosure, instead of fixing the rotational orientation of the guide tube relative to proximal joints and allowing the rotational position of the guide tube to be dictated by the kinematics of these other joints, an additional degree of freedom may be added to the robotic system. This additional degree of freedom would include automatic rotation about the central axis of the guide tube. Referring to FIG. 23, a motorized end effector 2302, a motor 2304, a rotational bearing 2306, and a guide tube 2308 may be used to provide automatic rotation. Automatic rotation may be accomplished by connecting guide tube 2308 to end effector 2302 with rotational bearing 2306 and driving the rotational position of guide tube 2308 with a rotational motor 2302, such as a servo motor. The position to which to drive the rotational motion of guide tube 2308 could be based on feedback from various types of sensors or from user input through software, as discussed in greater detail below.

There are several advantages to maintaining a desired orientation while moving down a trajectory line. For example, some types of surgical implants such as interbody cages are inserted in a particular orientation. A system to set and maintain the orientation of an implant at all points along the insertion trajectory would ensure that the implant was inserted in the proper final orientation and did not bind or seize on tissue or other instruments during insertion.

Another example of a situation in which a particular orientation is required while moving along a path other than a straight line is if the surgeon wants to trace or cut tissue at a particular orientation. For example, and as shown in FIGS. 22A-F, when cutting soft tissue with a scalpel or cutting bone with a bone scalpel, if a flat blade 2202 is perpendicular to the axis of the guide tube, it would be desirable to keep the flat cutting blade oriented in a certain way (i.e., tangent to the cut line).

The extra degree of freedom that rotates blade 2202 within the guide tube could automatically keep blade 2202 orientated as desired as the robot arm moves through the path of the intended cut. As illustrated in the figures, FIGS. 22A and 22D show an orientation of blade 2202 in a first position. FIGS. 22B and 22E show blade 2202 moving to a second position and FIGS. 22C and 22F show blade 2202 moving to a third position along the path.

As noted above, the robot system could operate to control this additional degree of freedom through several methods. A software input may fix the guide tube rotation at a particular position relative to the robot base, for example, 0°, 90°, 180°, 270° or any value from 0-360°. Through forward kinematics, the actual position of the guide tube relative to the robot base could be determined for any set of joint positions, and the rotational position of the guide tube then adjusted so that the rotational orientation of the guide tube remained fixed relative to the base at the value specified. Alternately, the rotational position that will be necessary to correctly orient a surgical implant when the guide tube is positioned where needed for a planned trajectory can be specified manually or automatically in software. Through inverse kinematics, the rotational position that the guide tube will be in at that position can be predicted. Then, the rotational position of the guide tube can be adjusted so that this target rotational position will be achieved once the robot arm has moved in place.

The additional rotational degree of freedom could also make use of feedback from tracking, such as the optical tracking of reflective spheres as described above. If the tracking system is registered to patient anatomy such as a CT scan, then through tracking of the patient and robot, software may automatically determine the necessary rotational position of the guide tube relative to the anatomy at any position of the robot to ensure that an implant is rotationally oriented as needed for implantation. For example, for an interbody implant, which is inserted in the disc space between two vertebral bodies, the angle of placement could be determined from drawing or automatically detecting from medical images the orientation of the disc space. This position would be set relative to the reference array on the patient and the guide tube rotation automatically updates to keep this angle fixed regardless of the position of the arm to ensure that the implant is inserted at the correct orientation.

Feedback from the tracking system may also use camera-based tracking of visible light patterns located on the guide tube. Trackable patterns could be artificially added to the guide tube, for example, by etching or printing lines on the guide tube, or patterns could be natural edges of the guide tube itself or extensions from the guide tube. Using tracked position feedback of the guide tube's orientation and location, the system could drive the rotational position of the guide tube into the desired rotation. For example, the system could ensure that the guide tube was properly aligned with the disc space for insertion of an interbody implant.

Figure 24:
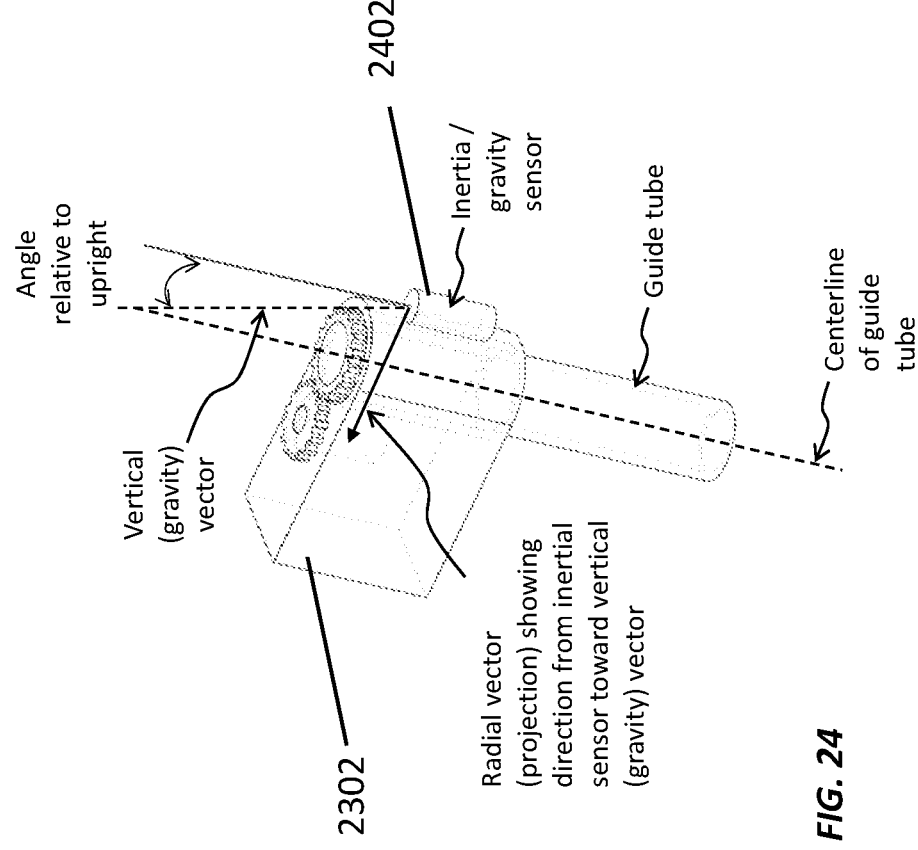

Referring FIG. 24, end effector 2302 may include an inertial sensor 2402. Another feedback method to maintain a fixed rotational orientation of the guide tube relative to the patient or the room is to use inertial or tilt sensor 2402. Such a sensor could detect the direction of gravity and direct the robot system to orient the guide tube to maintain a particular alignment relative to the gravity vector. For example, an inertial sensor that is offset radially from the centerline of the guide tube could provide feedback that directs the guide tube to always rotate into a position where the radial vector from the centerline of the guide tube through the sensor is oriented as closely with the line of gravity as is possible in the rotational degree of freedom. That is, there is a solution in the range of 0-360° of rotation of the guide tube where the angular difference between the gravity vector and the radial vector from guide tube center through the inertial sensor is smallest.

However, most straight-line trajectories into the body for surgical purposes have some angulation, and this method would be a simple way to keep the guide tube's rotational orientation fixed relative to the robot base while traveling along a straight line despite the normal rotation that would occur due to joint positions more proximal to the base.

Figure 25:
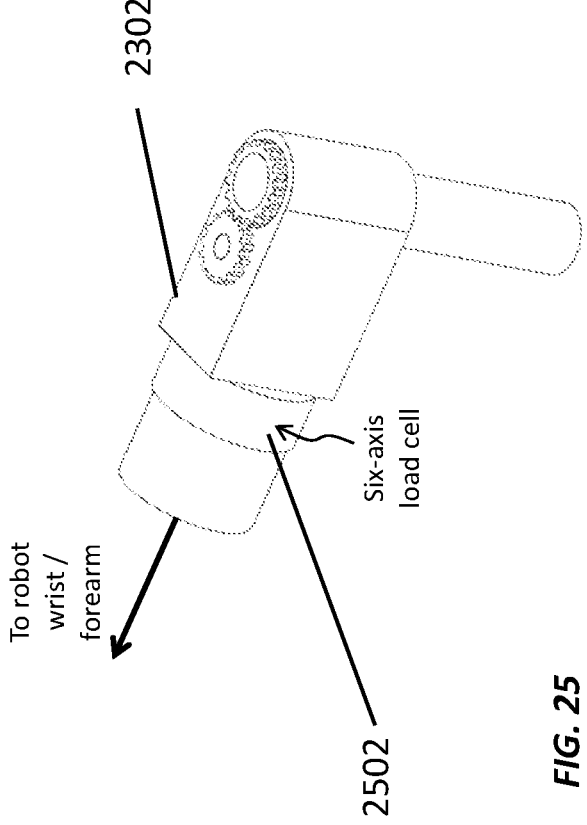

Referring to FIG. 25, end effector 2302 may include a force sensor 2502. Another feedback method to set a rotational orientation of the guide tube is force sensor 2502. Such a sensor would be effective in situations where the robot is used to perform some action perpendicular to the central axis of the guide tube, for example, cutting. Force magnitude and direction sensed from a force sensor that is embedded in the guide tube could be used to alter the rotational orientation of the guide tube to facilitate the procedure. For example, if the robot is moving laterally to cut or push through tissue, the direction of force could be sensed and the robot system could send an instruction to rotate the guide tube so that the sharpest edge is toward the direction of highest force.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A surgical robot system comprising:
a robot base;
a robot arm connected to and in electronic communication with the robot base;

a motorized end-effector connected to the robot arm and in electronic communication with the robot base, wherein the end-effector comprises a guide tube and is configured to receive a surgical instrument, wherein the guide tube comprises a central axis and is connected to the end-effector via a rotational bearing, and wherein the end-effector includes a servo motor for automatically rotating the guide tube;
an inertial sensor offset radially from the central axis of the guide tube, wherein the guide tube is configured to be automatically rotated to a fixed rotational orientation relative to a patient based on feedback from the inertial sensor; and
a force sensor embedded in the guide tube and configured to provide feedback to rotate the guide tube, wherein, based on feedback from the force sensor, the guide tube is configured to automatically rotate about the central axis of the guide tube to maintain a desired orientation of the guide tube as the robot arm and the end-effector are moved along a trajectory to a surgical site.

2. The surgical robot system of claim 1, wherein the guide tube is at a fixed angle relative to the robot base is configured to be automatically rotated to preserve the fixed angle relative to the robot base as the robot arm and the end-effector are moved.

3. The surgical robot system of claim 1, further comprising a tracking system to track the position of the end-effector.

4. The surgical robot system of claim 3, wherein the tracking system is configured to be registered to a patient anatomy.

5. A method of moving a surgical robot system relative to a patient comprising:
registering the surgical robot system of claim 1 to an anatomy of the patient;
moving the robot arm and the end-effector along a trajectory to the anatomy of the patient, wherein, based on feedback from the inertial sensor and the force sensor, the guide tube is automatically rotated about the central axis of the guide tube by the servo motor to maintain a desired orientation of the guide tube as the robot arm and end-effector are moved along the trajectory.

6. The method of claim 5, wherein the guide tube is at a fixed angle relative to the robot base and automatically rotates to preserve the fixed angle relative to the robot base as the robot arm and the end-effector are moved.

7. The method of claim 5, further comprising a tracking system to track the position of the end-effector.

8. The method of claim 7, wherein the tracking system is configured to be registered to a patient anatomy.

* * * * *